(12) United States Patent
Jha et al.

(10) Patent No.: US 10,812,380 B2
(45) Date of Patent: *Oct. 20, 2020

(54) MEDICAL DEVICE COMMUNICATION METHOD

(71) Applicant: ICU Medical, Inc., San Clemente, CA (US)

(72) Inventors: Prakash Kumar Arvind Jha, San Diego, CA (US); James Cudney, Santee, CA (US); Benjamin Herr, Kelso, WA (US); Mark I. Lee, Poway, CA (US); Matteo D. Picinich, Temecula, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/446,381

(22) Filed: Jun. 19, 2019

(65) Prior Publication Data
US 2020/0145332 A1 May 7, 2020

Related U.S. Application Data

(63) Continuation of application No. 15/581,442, filed on Apr. 28, 2017, now Pat. No. 10,333,843, which is a
(Continued)

(51) Int. Cl.
*H04L 12/741* (2013.01)
*H04L 12/725* (2013.01)
(Continued)

(52) U.S. Cl.
CPC .......... *H04L 45/74* (2013.01); *G06F 19/3418* (2013.01); *G16H 40/67* (2018.01);
(Continued)

(58) Field of Classification Search
CPC ........ H04L 45/74; H04L 69/32; H04L 69/162
See application file for complete search history.

(56) References Cited

U.S. PATENT DOCUMENTS 6,980,958 B1   12/2005   Surwit et al.
7,519,905 B2   4/2009    Kougiouris et al.
(Continued)

FOREIGN PATENT DOCUMENTS

CA   2 898 825   7/2014
CO   01110843    8/2003
(Continued)

OTHER PUBLICATIONS

"File Verification", Wikipedia.org, dated Oct. 11, 2011 in 2 pages, https://en.wikipedia.org/w/index.php?title=File_verification&oldid=455048290.
(Continued)

*Primary Examiner* — Gbemileke J Onamuti
(74) *Attorney, Agent, or Firm* — Knobbe Martens, Olson & Bear, LLP

(57) ABSTRACT

A medical device communication method that may be implemented within a variety of medical devices including but not limited to infusion pumps. The method may be implemented with a protocol stack for at least intra-device communication. Embodiments provide connection-oriented, connectionless-oriented, broadcast and multicast data exchange with priority handling of data, fragmentation, and reassembly of data, unique static and dynamic address assignment and hot swap capability for connected peripherals or subsystems.

17 Claims, 19 Drawing Sheets

Related U.S. Application Data continuation of application No. 14/198,807, filed on Mar. 6, 2014, now Pat. No. 9,641,432.

(60) Provisional application No. 61/773,647, filed on Mar. 6, 2013.

(51) Int. Cl.
  *H04L 29/06* (2006.01)
  *H04L 29/08* (2006.01)
  *G16H 40/67* (2018.01)
  *G06F 19/00* (2018.01)

(52) U.S. Cl.
  CPC ............ *H04L 45/302* (2013.01); *H04L 69/16* (2013.01); *H04L 69/162* (2013.01); *H04L 69/165* (2013.01); *H04L 69/32* (2013.01)

(56) References Cited

U.S. PATENT DOCUMENTS

| | | |
|---|---|---|
| 8,489,427 B2 | 7/2013 | Simpson et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 2001/0048027 A1 | 12/2001 | Walsh |
| 2002/0143580 A1 | 10/2002 | Bristol et al. |
| 2002/0173702 A1 | 11/2002 | Lebel et al. |
| 2004/0104271 A1 | 6/2004 | Martucci et al. |
| 2005/0102165 A1 | 5/2005 | Oshita et al. |
| 2007/0061393 A1 | 3/2007 | Moore |
| 2010/0174266 A1 | 7/2010 | Estes |
| 2010/0209268 A1 | 8/2010 | Davis |
| 2011/0138185 A1 | 6/2011 | Ju et al. |
| 2011/0231216 A1 | 9/2011 | Fyke et al. |
| 2013/0204188 A1 | 8/2013 | Kamen et al. |
| 2013/0346108 A1 | 12/2013 | Kamen et al. |
| 2014/0163517 A1 | 6/2014 | Finan et al. |
| 2014/0180711 A1 | 6/2014 | Kamen et al. |
| 2014/0266790 A1 | 9/2014 | Al-Ali et al. |
| 2016/0015885 A1 | 1/2016 | Pananen et al. |
| 2016/0034655 A1 | 2/2016 | Gray et al. |
| 2017/0262590 A1 | 9/2017 | Karakosta et al. |
| 2018/0121613 A1 | 5/2018 | Connely, IV et al. |
| 2019/0096518 A1 | 3/2019 | Pace |
| 2019/0147998 A1 | 5/2019 | Ruchti et al. |
| 2019/0228863 A1 | 7/2019 | Dharwad et al. |
| 2019/0240405 A1 | 8/2019 | Wehba et al. |
| 2019/0243829 A1 | 8/2019 | Butler et al. |
| 2019/0269852 A1 | 9/2019 | Kohlbrecher |

FOREIGN PATENT DOCUMENTS

| | | |
|---|---|---|
| JP | 07-502678 | 3/1995 |
| JP | 11-500643 | 1/1999 |
| JP | 2000-316820 | 11/2000 |
| JP | 2002-531154 | 9/2002 |
| JP | 2006-520949 | 9/2006 |
| JP | 2007-518479 | 7/2007 |
| JP | 2008-080036 | 4/2008 |
| JP | 2008-516303 | 5/2008 |
| JP | 2008-529675 | 8/2008 |
| JP | 2009-163534 | 7/2009 |
| JP | 2010-502361 | 1/2010 |
| JP | 2012-070991 | 4/2012 |
| WO | WO 2015/124569 | 8/2015 |

OTHER PUBLICATIONS

Gabel et al., "Camp: A Common API for Measuring Performance", 21st Large Installations System Administration Conference (LISA '07), 2007, pp. 49-61.
International Preliminary Report on Patentability and Written Opinion received in PCT Application No. PCT/US2014/021335, dated Sep. 17, 2015 in 12 pages.
International Search Report and Written Opinion received in PCT Application No. PCT/US2014/021335, dated Jul. 8, 2014 in 13 pages.
"Software Versioning", Wikipedia.org, dated Oct. 16, 2011 in 11 pages, https://en.wikipedia.org/w/index.php?title=Software_versiioning&oldid=455859110.
Sutton et al., "The Syntax and Semantics of the PROforma Guideline Modeling Language", Journal of the American Medical Informatics Association, Sep./Oct. 2003, vol. 10, No. 5, pp. 433-443.

Session Layer Internals

Control Flags
1. Layer Flag [1 bit]
2. Connection Type [2 bits]
3. CID Source [1 bit]

| Connection Type | Destination Address | Destination Port | Source Port | CID | File Descriptor |
|---|---|---|---|---|---|
| Service | 8 | 50 | 40 | 100 | 55 |
| TCP | 5 | 23 | 60 | 72 | 63 |
| Service | 15 | 68 | 40 | 110 | 87 |
| TCP | 4 | 20 | 55 | 103 | 21 |

FIG. 10B

Connection Oriented Data Transfer

| Layer Flag [1 bit] | Connection Type [2 bits] | Message Type [4 bits] | CID | Data |
|---|---|---|---|---|
| 0 | Connection Oriented | Data | 1 Byte | N Bytes |

Connectionless Data Transfer

| Layer Flag [1 bit] | Connection Type [2 bits] | Message Type [4 bits] | Source Port | Destination Port | Data |
|---|---|---|---|---|---|
| 0 | Connection Less | Data | 1 Byte | 1 Byte | N Bytes |

Connection Request

| Layer Flag [1 bit] | Connection Type [2 bits] | Message Type [4 bits] | Command [1 Byte] | Source Port | Destination Port |
|---|---|---|---|---|---|
| 1 | Unknown | Connection | Connection Request | 1 Byte | 1 Byte |

Connection Accept

| Layer Flag [1 bit] | Connection Type [2 bits] | Msg. Type [4 bits] | Command [1 Byte] | CID | Destination Port | Source Port |
|---|---|---|---|---|---|---|
| 1 | Unknown | Connection | Connection Accept | 1 Byte | 1 Byte | 1 Byte |

Connection Acknowledgement

| Layer Flag [1 bit] | Connection Type [2 bits] | Message Type [4 bits] | Command [1 Byte] | CID | Source Port |
|---|---|---|---|---|---|
| 1 | Unknown | Connection | Connection Ack. | 1 Byte | 1 Byte |

Connection Disconnect

| Layer Flag [1 bit] | Connection Type [2 bits] | Message Type [4 bits] | Command [1 Byte] | CID | Source Port |
|---|---|---|---|---|---|
| 1 | Unknown | Connection | Connection Disconnect | 1 Byte | 1 Byte |

Connection Disconnect Ack

| Layer Flag [1 bit] | Connection Type [2 bits] | Message Type [4 bits] | Command [1 Byte] | CID | Source Port |
|---|---|---|---|---|---|
| 1 | Unknown | Connection | Connection Disconnect Ack | 1 Byte | 1 Byte |

FIG. 10C

Connection Reject

| Layer Flag [1 bit] | Connection Type [2 bits] | Msg. Type [4 bits] | Command [1 Byte] | Destination Port | Source Port | Reason |
|---|---|---|---|---|---|---|
| 1 | Unknown | Connection | Connection Reject | 1 Byte | 1 Byte | 1 Byte |

CID Info Request

| Layer Flag [1 bit] | Connection Type [2 bits] | Message Type [4 bits] | Command [ 1 Byte] | CID | Source Port |
|---|---|---|---|---|---|
| 1 | Unknown | CID | CID Info Request | 1 Byte | 1 Byte |

CID Info Response

| Layer Flag [1 bit] | Conn. Type [2 bits] | Msg. Type [4 bits] | Command [1 Byte] | CID | Source Port | Info Length [1 Byte] | CID Info |
|---|---|---|---|---|---|---|---|
| 1 | Unknown | CID | CID Info Response | 1 Byte | 1 Byte | 1 Byte | 1 Byte |

Socket Status Request

| Layer Flag [1 bit] | Conn. Type [2 bits] | Message Type [4 bits] | Command [ 1 Byte] | CID | Source Port |
|---|---|---|---|---|---|
| 1 | Unknown | Socket | Socket Status Request | 1 Byte | 1 Byte |

Socket Status Response

| Layer Flag [1 bit] | Conn. Type [2 bits] | Msg. Type [4 bits] | Command [1 Byte] | CID | Source Port | Info Length [1 Byte] | Socket Status |
|---|---|---|---|---|---|---|---|
| 1 | Unknown | Socket | Socket Status Res | 1 Byte | 1 Byte | 1 Byte | 1 Byte |

Subscribe To Service

| Layer Flag [1 bit] | Connection Type [2 bits] | Message Type [4 bits] | Command [ 1 Byte] | Source Port | Destination Port |
|---|---|---|---|---|---|
| 1 | Unknown | Service | Subscription Request | 1 Byte | 1 Byte |

Subscription To Service Ack

| Layer Flag [1 bit] | Connection Type [2 bits] | Msg. Type [4 bits] | Command [1 Byte] | CID | Destination Port | Source Port |
|---|---|---|---|---|---|---|
| 1 | Unknown | Service | Subscription Ack | 1 Byte | 1 Byte | 1 Byte |

FIG. 10D

Subscription Reject

| Layer Flag [1 bit] | Conn. Type [2 bits] | Msg. Type [4 bits] | Command [1 Byte] | Destination Port | Source Port | Reason |
|---|---|---|---|---|---|---|
| 1 | Unknown | Service | Subscription Reject | 1 Byte | 1 Byte | 1 Byte |

Unsubscribe From Service

| Layer Flag [1 bit] | Conn. Type [2 bits] | Msg. Type [4 bits] | Command [ 1 Byte] | CID | Source Port |
|---|---|---|---|---|---|
| 1 | Unknown | Service | Unsubscribe Request | 1 Byte | 1 Byte |

Unsubscribe From Service Ack

| Layer Flag [1 bit] | Conn. Type [2 bits] | Msg. Type [4 bits] | Command [ 1 Byte] | CID | Source Port |
|---|---|---|---|---|---|
| 1 | Unknown | Service | Unsubscribe Request Ack | 1 Byte | 1 Byte |

Device Address Request

| Layer Flag [1 bit] | Conn. Type [2 bits] | Msg. Type [4 bits] | Command [ 1 Byte] | CID | Source Port |
|---|---|---|---|---|---|
| 1 | Unknown | Device Info | Device Address Request | 1 Byte | 1 Byte |

Device Address Response

| Layer Flag [1 bit] | Conn. Type [2 bits] | Msg. Type [4 bits] | Command [1 Byte] | CID | Source Port | Info Length [1 Byte] | Device Address |
|---|---|---|---|---|---|---|---|
| 1 | Unknown | Device Info | Device Addr. Resp. | 1 Byte | 1 Byte | 1 Byte | 1 Byte |

Device Type Request

| Layer Flag [1 bit] | Conn. Type [2 bits] | Msg. Type [4 bits] | Command [ 1 Byte] | CID | Source Port |
|---|---|---|---|---|---|
| 1 | Unknown | Device Info | Device Type Request | 1 Byte | 1 Byte |

Device Type Response

| Layer Flag [1 bit] | Conn. Type [2 bits] | Msg. Type [4 bits] | Command [1 Byte] | CID | Source Port | Info Length [1 Byte] | Device Name |
|---|---|---|---|---|---|---|---|
| 1 | Unknown | Device Info | Device Type Response | 1 Byte | 1 Byte | 1 Byte | 1 Byte |

FIG. 11A
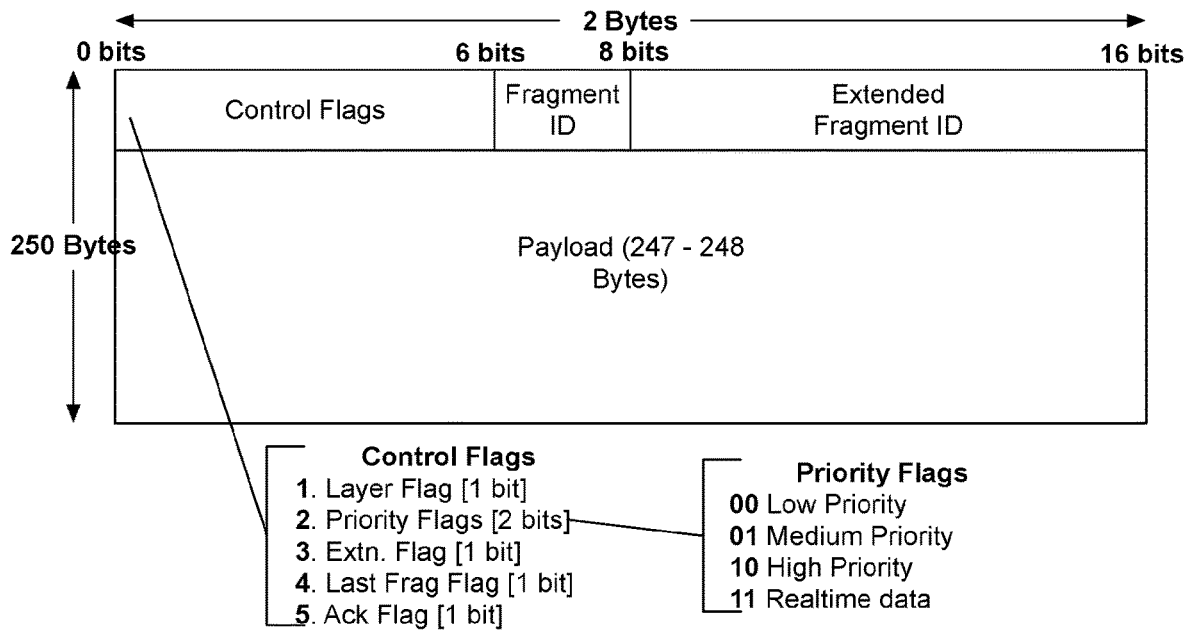
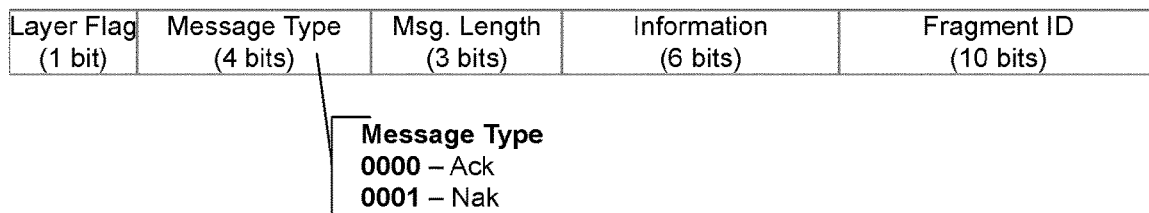
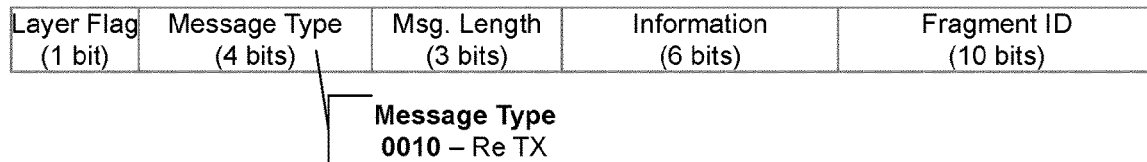
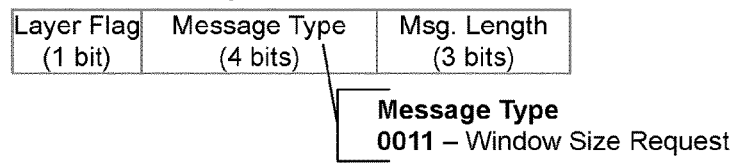

FIG. 11B
Window Size Response
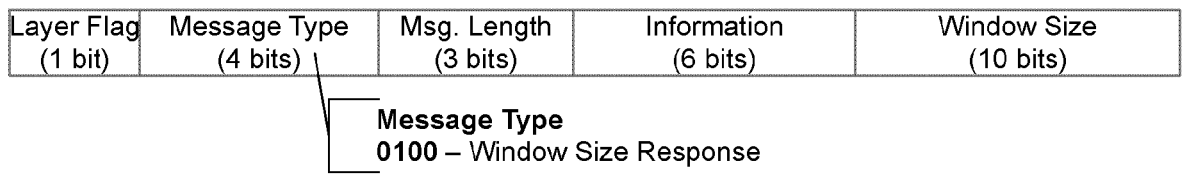
Ping
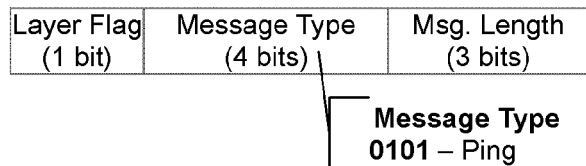
Ping Response
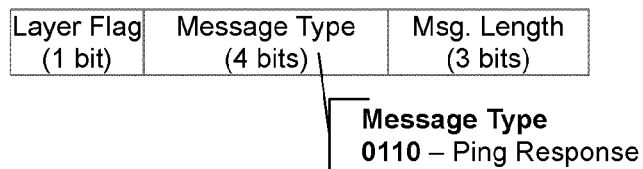
Intent
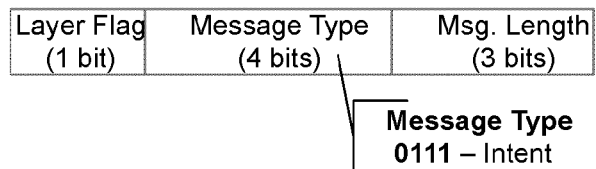

FIG. 12A

Physical Layer Internals

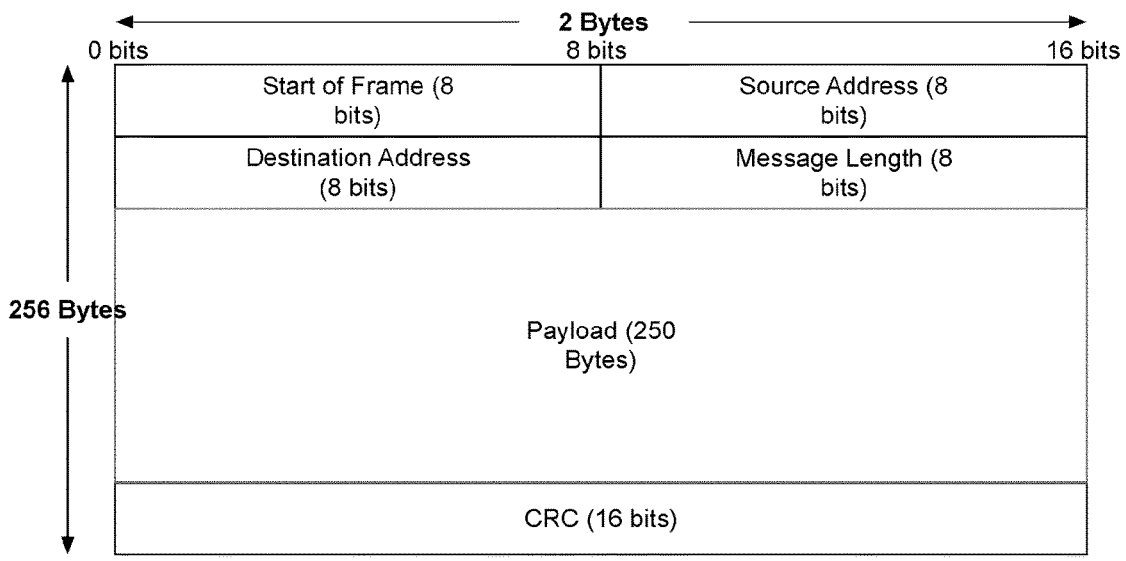

| Bus Interface | Device ID | HW Address | Device Type | Device Status | Status Duration | Last Updated |
|---|---|---|---|---|---|---|
| Serial | 10 | 23:ad:33:56 | CE | Online | 0 | 112548 |
| CAN | 20 | 44:56:ac:eb | PMC1 | Pumping | 0 | 125489 |
| CAN | 50 | 44:56:ef:bd | PMC2 | Sleep | 100254 | 095446 |

Address Request Message

| SOF | Destination Address | Source Address | Message Length | Message Type | Physical Address | CRC |
|---|---|---|---|---|---|---|
| 1 Byte | 01 | 00 | 2 | Address Request | 1 Byte | 2 Bytes |

Address Response Message

| SOF | Destination Address | Source Address | Message Length | Message Type | Physical Address | Logical Address | CRC |
|---|---|---|---|---|---|---|---|
| 1 Byte | 00 | 01 | 3 | Address Response | 1 Byte | 1 Byte | 2 Bytes |

FIG. 12B

Disassociation Message

| SOF | Destination Address | Source Address | Message Length | Message Type | CRC |
|---|---|---|---|---|---|
| 1 Byte | 01 | 1 Byte | 1 | Disconnect. Request | 2 Bytes |

Request Device Type Message

| SOF | Destination Address | Source Address | Message Length | Message Type | CRC |
|---|---|---|---|---|---|
| 1 Byte | 1 Byte | 1 Byte | 1 | Device Type Request | 2 Bytes |

Device Type Response Message

| SOF | Destination Address | Source Address | Message Length | Message Type | Device Type | CRC |
|---|---|---|---|---|---|---|
| 1 Byte | 1 Byte | 1 Byte | 2 | Device Type Response | 1 Byte | 2 Bytes |

Device Status Request Message

| SOF | Destination Address | Source Address | Message Length | Message Type | CRC |
|---|---|---|---|---|---|
| 1 Byte | 1 Byte | 1 Byte | 1 | Device Status Req. | 2 Bytes |

Device Status Response Message

| SOF | Destination Address | Source Address | Message Length | Message Type | Device Status | CRC |
|---|---|---|---|---|---|---|
| 1 Byte | 1 Byte | 1 Byte | 2 | Device Status Resp. | 1 Byte | 2 Bytes |

Device Status Duration Message

| SOF | Destination Address | Source Address | Message Length | Message Type | Device Status | CRC |
|---|---|---|---|---|---|---|
| 1 Byte | 1 Byte | 1 Byte | 2 | Status Duration | 1 Byte | 2 Bytes |

Data Re-Transmission Request Message

| SOF | Destination Address | Source Address | Message Length | Message Type | CRC |
|---|---|---|---|---|---|
| 1 Byte | 1 Byte | 1 Byte | 1 | Data ReTransmis. | 2 Bytes |

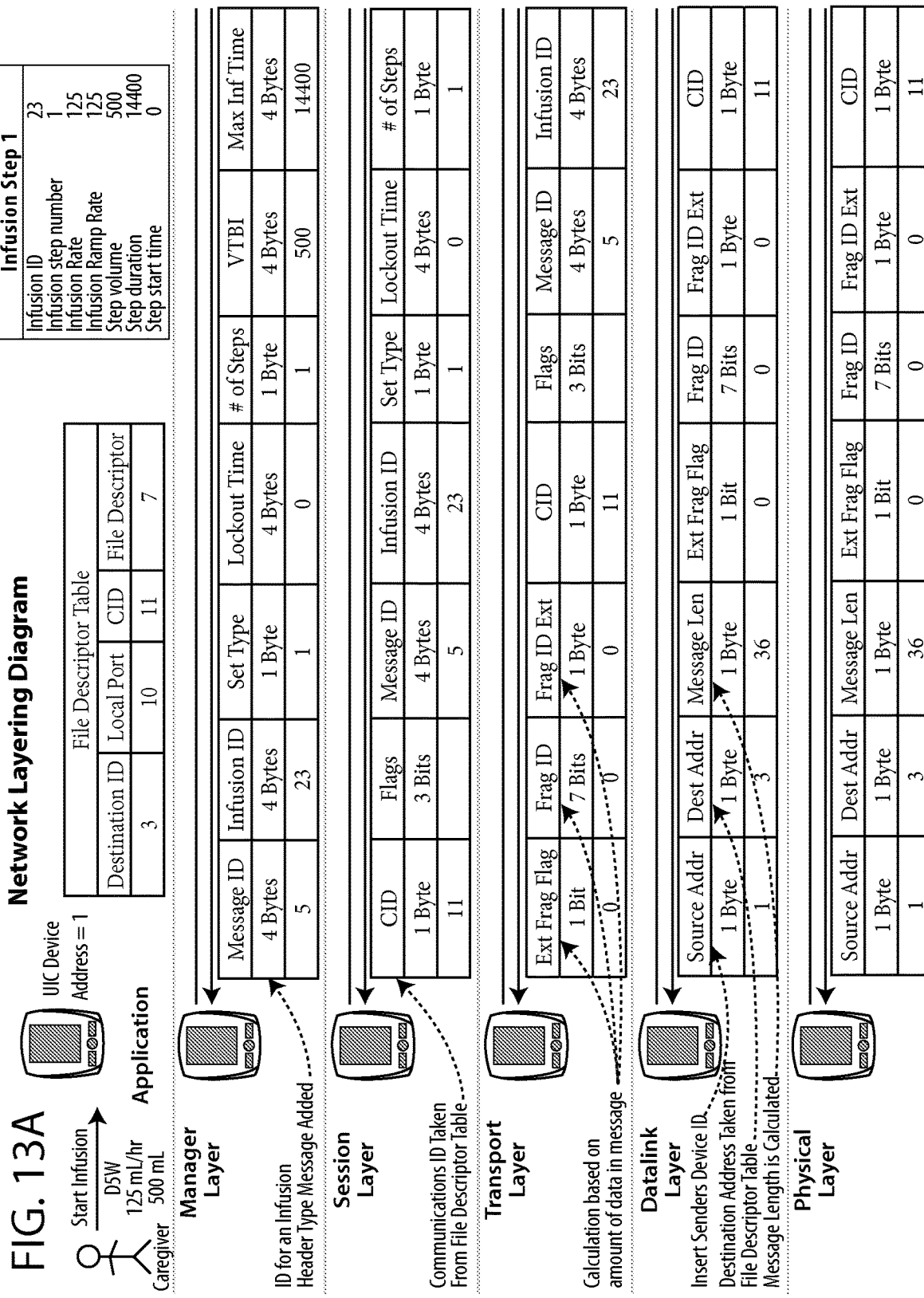

MEDICAL DEVICE COMMUNICATION METHOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

One or more embodiments of the invention are related to the field of multiplex communication protocols for medical devices such as, but not limited to, infusion pumps. More particularly, but not by way of limitation, embodiments of the invention enable a medical device communication method for communication between connected peripherals and subsystems that includes connection-oriented, connectionless-oriented, broadcast and multicast data exchange with priority handling of data, fragmentation and reassembly of data, unique static and dynamic address assignment and hot swap capabilities.

Description of the Related Art

Devices that exchange data generally do so using a communication protocol. Communication protocols enable data to be transmitted and received in a controlled manner. Medical devices are example devices that may utilize a communication protocol, for example to exchange data between peripherals or subsystems that generate or utilize data. There are many types of communications protocols that vary in complexity, efficiency and hardware utilization. Current communication protocols utilized within medical devices make use of the operating system and particular bus architecture within the medical device. A problem with this type of architecture is that some implementations may prevent time-multiplexed access of the communication link, thereby starving or otherwise preventing multiple applications from communicating simultaneously. In addition, applications that transfer data using operating system and bus specific software calls must be altered when the operating system or bus architecture changes, specifically to account for differences in operating system calls or with respect to the bus architecture, different data formatting, sequencing and any other protocol specific nuances. In addition, medical devices in general must undergo extensive testing to ensure that they do not fail. Thus, changing bus architectures increases costs associated with applications that make use of the bus architecture, since the application must be retested if the source code for the application is altered.

Known communications protocols are generally targeted at a specific type of communication bus architecture, for example Ethernet, WiFi, Bluetooth, CAN, Serial, I2C, SPI, etc. Known communication protocols in general are not capable of use with more than one type of communication bus since they attempt to provide a solution to a specific communication problem in a coherent manner. Because of the low power requirements, limited processor capabilities and limited memory capacity of medical devices with embedded processors that do specific functions or tasks, such as infusion pumps, existing sophisticated communications protocols are generally not utilized in such medical devices.

In summary, known solutions use communication protocols that are tied to a specific operating system and/or communications bus. Unfortunately, these communication protocols are not agnostic to all communication bus types and do not provide an efficient and lightweight protocol stack for intra-device communication that includes connection-oriented, connectionless-oriented, broadcast and multicast data exchange with priority handling of data, fragmentation, and reassembly of data, unique static and dynamic address assignment for connected subsystems and hot swap capabilities. For at least the limitations described above there is a need for a medical device communication method that provides these features as described and claimed herein.

SUMMARY OF THE INVENTION

Embodiments of the invention enable a medical device communication method for communication between medical peripherals and subsystems that includes connection-oriented, connectionless-oriented, broadcast and multicast data exchange with priority handling of data, fragmentation and reassembly of data, unique static and dynamic address assignment and hot swap capabilities. Example medical devices that may employ an embodiment of the invention include but are not limited to infusion pumps, both present and future. Embodiments of the communication protocol provide an interface that is detached, or otherwise abstracted from the operating system and underlying bus architecture within the medical device, making the behavior and interface of communication protocol consistent across bus architectures and operating systems, which is unknown in the art of infusion pumps for example. Hence, the same application may be utilized on multiple hardware platforms, for example without altering the application itself. Thus, embodiments enable simplified application code, portability thereof and minimize maintenance and testing requirements. Embodiments may utilize any type of physical communication path, for example wireless or hardwired, including but not limited to a data bus. Embodiments for intra-device communications over a data bus generally employ data bus drivers specific to each type of data bus to control reading and writing of data over the bus along with a standard interface to these data bus drivers.

Embodiments may be implemented in separate layers of software configured to execute on one or more computing elements, wherein each layer performs operations to provide data exchange that is generally independent of the other layers. Each layer for example may create, read or update headers associated with data to be exchanged, wherein the headers contain information to support the above-mentioned features. The layers make up what is known as a protocol stack. Embodiments of the protocol stack may include a manager layer, session layer, transport layer, and data link layer or any other architecture as long as the resulting implementation provides the functionality described herein.

Depending on the peripheral or subsystem, data type, priority and desired reliability of data to be exchanged, applications may transmit data using connection-oriented data exchange to provide guaranteed delivery of data or connectionless data exchange for less sensitive data. Embodiments also support one-to-one, as well as one-to-many and many-to-one multicast, and broadcast modes of data exchange between connected peripherals and subsystems. At least one embodiment also supports priority based data exchange and gives preference to high priority data over low priority data to ensure that high priority messages are delivered first. Additionally, at least one embodiment supports data fragmentation and reassembly data to comply with demands of the particular physical communication technology. Embodiments also provide unique static and dynamic address assignment for connected subsystems and hot swap capabilities, which are unknown for example in current infusion pumps.

Specifically, in the case of connection-oriented communication, at least one embodiment utilizes a Communication ID or "CID", as a token to uniquely identify all active connections within a subsystem and route the data between respective applications. In the case of connectionless communications, at least one embodiment uses port numbers, for example source and destination port numbers, to identify the targeted application. At least one embodiment supports subscription services for recipient applications, which enables multicasting of data to all subscribed applications. Multicasting can be both connection-oriented and connectionless. In connection-oriented communication sessions, at least one embodiment guarantees delivery of data, for example using acknowledgements. Alternatively, connectionless communication sessions do not guarantee delivery of data, but are very efficient. At least one embodiment supports broadcasting of data/messages, wherein the broadcast messages are forwarded to all the subsystems connected to the broadcasting subsystem.

Applications may need to exchange data larger in size than an underlying communication technology or data bus can support. In such cases, at least one embodiment breaks or fragments the data into a smaller size, for example that the data bus can actually transfer. At least one embodiment reassembles data into the original data size at the receiving end. At least one embodiment executes on embedded systems that may have limited resources, including memory, processing power, bus utilization, and power. Hence, embodiments efficiently utilize available resources. Example data exchanges that are large enough to warrant fragmentation of messages include drug library downloads and firmware updates.

With respect to fragmentation, at least one embodiment utilizes window that represents a count of fragments that may be sent before receiving an acknowledgement from receiver. In at least one embodiment, the transmitter requests for window size from the receiver before sending the first fragment. The receiver determines the available memory space to accommodate received packets and responds with the window size, for example as an integral multiple of the maximum frame size that fits into the available memory. The transmitter numbers the fragments in sequence and sends them to receiver. After a window size worth of messages have been sent, the transmitter waits for an acknowledgement of the last fragment. The receiver accumulates all the received fragments and verifies that all the received fragments are in sequence. If there is no missing fragment, the receiver sends the fragment number of last fragment as an acknowledgement, or otherwise sends the fragment numbers of missing fragments as part of negative acknowledgement or NAK.

Since medical devices such as infusion pumps in the future may include hot swappable peripherals or subsystems, at least one embodiment supports unique address assignments to connected devices in order to provide conflict free exchange of data, thus reducing complexity in applications. At least one embodiment supports communication over multiple underlying data transfer technologies such as serial, CAN, SPI, SDIO, USB, or any other type of physical medium or data bus. At least one embodiment also keeps track of devices connected on each bus and routes data onto the respective bus.

BRIEF DESCRIPTION OF THE DRAWINGS

The above and other aspects, features and advantages of the invention will be more apparent from the following more particular description thereof, presented in conjunction with the following drawings wherein:

FIGS. 10A-D illustrate the structure of the messages of the Session Layer.

FIGS. 11A-B illustrate the structure of the messages of the Transport Layer.

FIGS. 12A-B illustrate the structure of the messages of the Data Link/Physical Layer.

FIGS. 13A-B illustrate an exemplary message transfer of a medical function using exemplary values within the messages to demonstrate the system and method according to at least one embodiment of the invention.

DETAILED DESCRIPTION OF THE PREFERRED EMBODIMENT

A medical device communication method will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
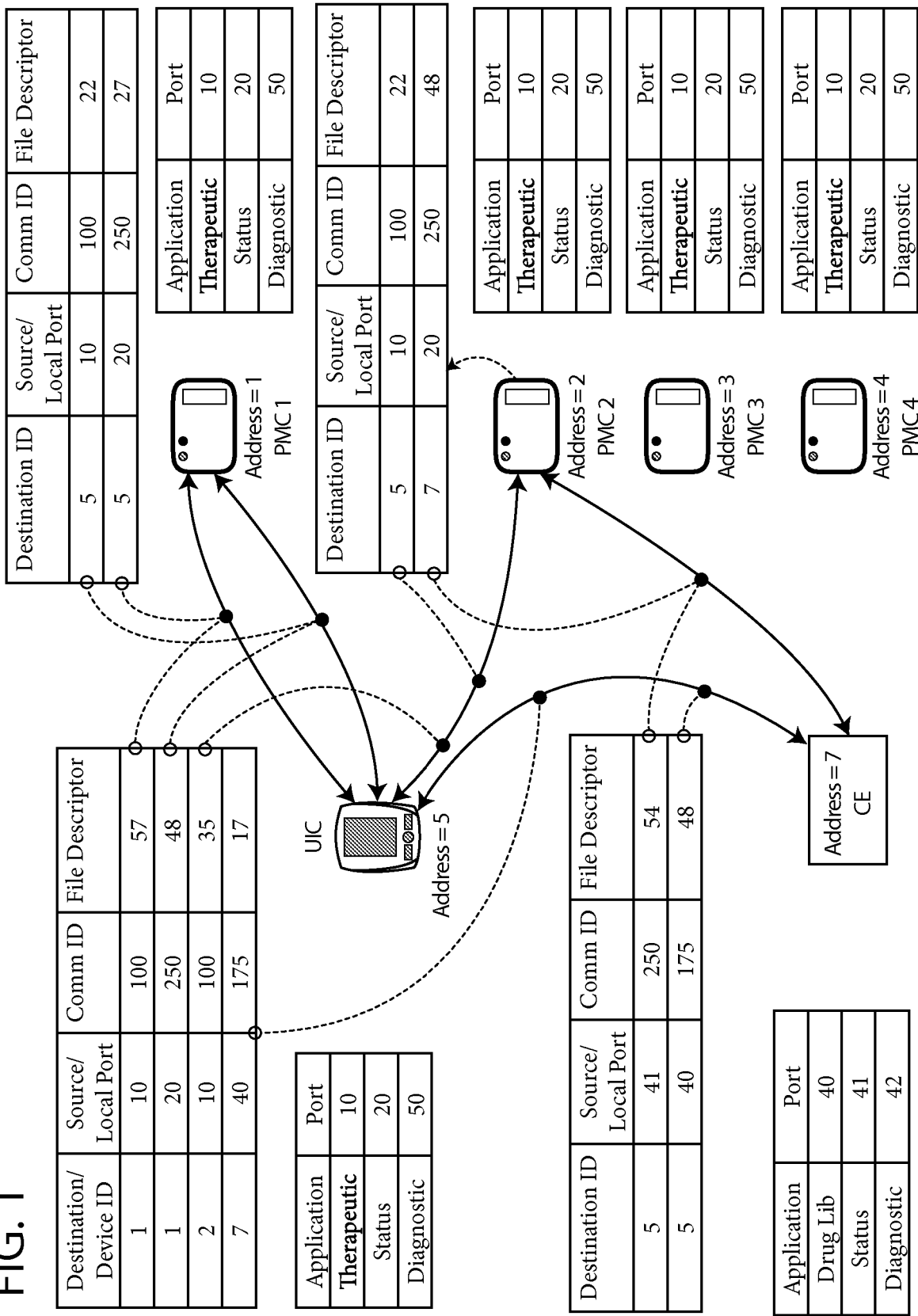
FIG. 1 illustrates an architectural view of a system having a user interface controller, and multiple peripherals that communicate with one another using an embodiment of the invention.

FIG. 1 illustrates an architectural view of a system having user interface controller or "UIC", and multiple peripherals that communicate with one another using an embodiment of the invention. As shown user interface controller UIC communicates with peripherals Pump Motor Control or "PMC", PMC 1 and PMC 2 as well as communication engine or "CE" for various applications including but not limited to drug library, status and diagnostic message handling. For exemplary purposes, UIC has a destination/device ID, e.g., an address of 5 and messages from UIC to the other devices travel over pathways uniquely defined by the tuples defined in the table, for example on a per device and communication ID defined channel. These channels are shown in the table above UIC, namely between UIC and PMC 1, at ports 10 and 20, i.e., the therapeutic and status ports, via Communication ID or "CID" 100 and CID 250 respectively followed by a channel used between UIC and PMC 2 at port 10, the therapeutic port, via Communication ID 100, along with a channel between UIC and CE at port 40, via Communication ID 175. The CE, whose address is 7, shows channels in the table above CE to PMC 2 and the UIC, namely devices 2 and 5 via Communication ID's 250 and 175 respectively. PMC 1 is illustrated as having channels to the UIC, via Communication ID's 100 and 250. PMC 2 is illustrated as having channels to the UIC and CE through ports 10 and 20, via Communication ID's 100 and 250. PMC 3 and 4 may be hot swapped into the system or otherwise commanded or queried on the fly. Embodiments of the invention are generally configured to utilize minimal memory and processing to enable execution on devices having limited memory and limited processing power, which is generally unknown in the art with respect to sophisticated communications protocols for example. In one or more embodiments, the stack utilizes one kernel thread to execute the Data Link layer and Transport lower layer, whereas remaining layers are part of application process and execute in the context of application. Minimum thread implementation supports blocking access, for example read and write operations block until the operation is completed. Embodiments may also support asynchronous callbacks, and in such cases, the stack may utilize two threads, one for write operations and one for read operation, hence total number of threads utilized is 2*N+1, where N is the number of applications using the stack.

Figure 2:
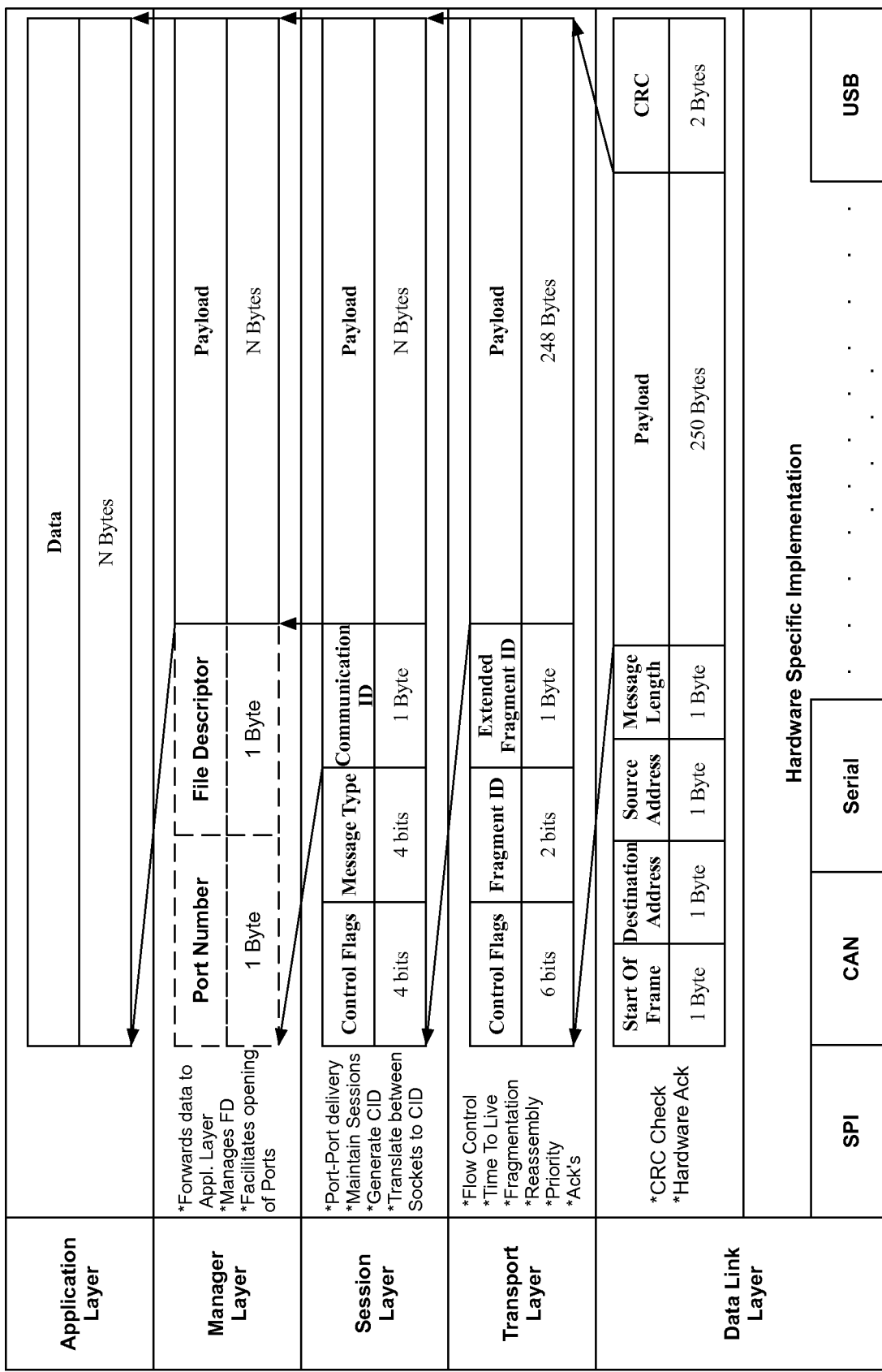
FIG. 2 illustrates a hierarchical layered embodiment of the invention implemented as a protocol stack.

FIG. 2 illustrates a hierarchical layered embodiment of the invention implemented as a protocol stack. As shown, a data message in the application layer is N bytes long. The application layer may include any functionality independent of the protocol stack that is implemented in the layers beneath the application layer as shown. When the message is transmitted from one application to another, for example to an application executing on a peripheral or subsystem, control information or headers are appended to the message as the message descends layers. The various headers or other appended information are removed as the message rises through the protocol stack to the respective receiving application.

In one or more embodiments, a manager layer may be utilized to implement the first layer in the protocol stack beneath the application. The manager layer may provide standard interfaces to applications across any desired operating system. The layer provides application programmer interfaces or API's that enables socket-based communications between applications. The manager layer also manages file descriptors and facilitates opening of ports. In at least one embodiment, the manager layer creates and otherwise utilizes a message header having a port number and file descriptor.

Figure 10A:
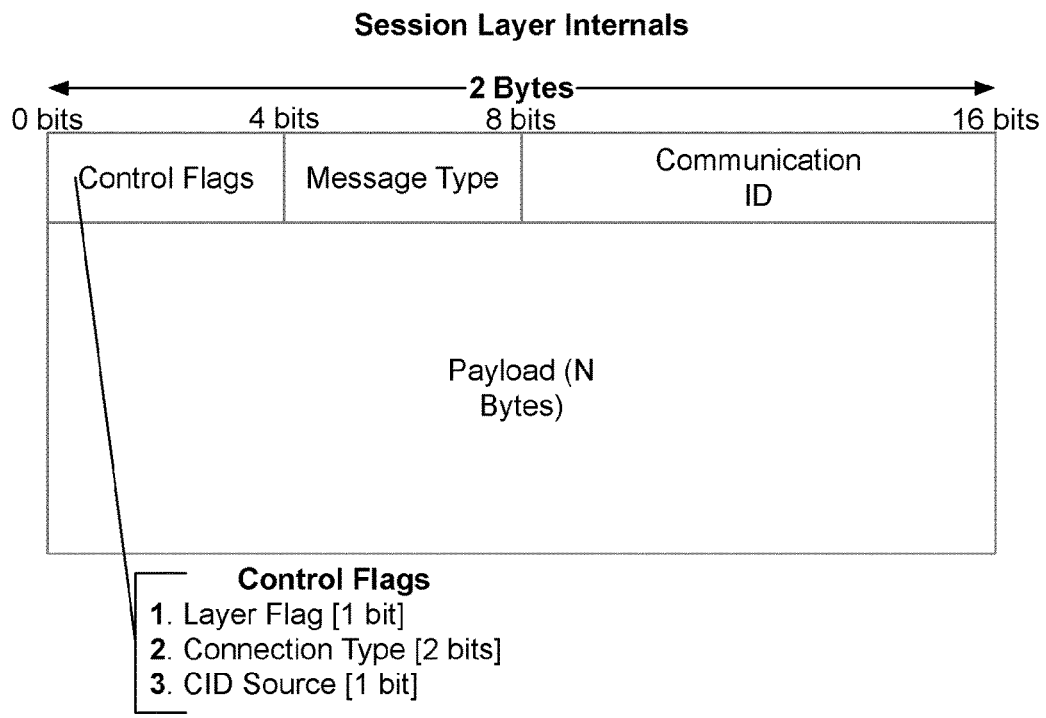

A session layer is another layer in the protocol stack and provides or includes API's to exchange data and control between manager layer and session layer. The session layer may provide guaranteed application-to-application delivery of data and enables connection-oriented and connectionless-oriented modes of communication. This layer also enables one-to-one, one-to-many, many-to-one multicast and broadcasting mode of communication. The layer maintains the translation between CID and an associated socket or virtual port. For connection-oriented communication, the protocol utilizes the CID and otherwise generates and utilizes CID's. As the connection-oriented data exchange utilizes a handshake between applications for data exchange, the session layer handles the handshake and generates a CID for the communication and informs the other participating session layers of application(s) about the CID. After the handshake, data packets utilize the CID for communication. In case of connectionless communication, no CID is utilized and hence both source and destination port addresses are exchanged in each communication packet or payload. In at least one embodiment, the manager layer creates and otherwise utilizes a message header having control flags and a message type along with a communication identifier. This structure along with an exemplary connection table is shown in FIG. 10A, along with exemplary message types in FIGS. 10B-D. The control flags may be implemented with a layer flag of 1 bit, a connection type of 2 bits and a CID source of 1 bit for example. The session layer utilizes some messages that are associated with the session-session communications and are never passed up the stack to the manager layer in one or more embodiments. These messages are generally used for establishing or closing connections, acknowledgements, etc. If the layer flag is set, for example set to True or 1, the message will be consumed at session layer and will not be forwarded up the stack. The connection type flag indicates the type of connection, for example if connection-oriented, set to 01 or if connectionless, set to 00. An example connectionless protocol is User Datagram Protocol or UDP while an example connection-oriented protocol is Transmission Control Protocol or TCP. The CID source bit is used to identify if the data as being sent from the entity that generated CID for the connection in use or from sub-modules using this CID for communication. The entity that generates CID for communication sets this bit for all the messages generated by it for the respective active connection, while other entities involved in communication reset this flag for messages while using this CID. As the CID is unique within the entity generating CID, there may be duplicate CIDs across other entities. Hence, this layer helps in resolving the source of CID (local or remote) via this flag. The message type field associates messages with categories and lets the session layer know what to expect in the following fields. The message type field is a 4-bit wide field in one or more embodiments. The message type field is used to determine the type of message. Exemplary values include 0000 for data, 0001 for connection, 0010 for CID, 0011 for socket, 0100 for service and 0101 for device information. Any module that provides a service generates a unique CID for communicating with the consumers of the service. Communication ID '0' is reserved for connectionless type of communication in one or more embodiments. Communication ID field is 1 byte wide and is utilized for the data that is passed up the protocol stack. CID can hold any number between 0-255. As state above, CID '0' is for connectionless type communication and is thus not a valid ID for connection-oriented communication. Connection oriented type communications will have a CID in the range of 1-255. Hence, CID '0' is an implicit indication of connectionless communication, any other number between 1-255 suggests connection-oriented. Applications may establish one or more notification filters to select message to receive and process using a desired function. The filtration mechanism may utilize one or more regular expression that specifies the location, length and content of the matching data in the data portion of the packet. This functionality is implemented in the management layer in one embodiment of the invention. Before the management layer forwards the data to application, it may check if any filters are defined on the data. Depending on the filter, the manager layer filters data and forwards the data to respective callback handlers.

Embodiments of the invention enable a single application to maintain connections with more than one device over one or more physical communication layers or bus implementations. This is accomplished by the use of virtual ports. A single application such as the Therapeutic Manager in the UIC may for example maintain open connections with more than one drug pump PMC or other device as would be asserted during a multi-channel infusion. Similarly, many applications may maintain a connection with one application or device, for example, UIC, CE, and other applications may connect to a particular PMC to gather infusion status information.

The one-to-many and/or many-to-one communication relationship can further be classified into three types, unicast, multicast and broadcast. For example, different applications can gather infusion status from a PMC either by requesting, for example via multicasting, or the PMC can broadcast its status on a known port and interested applications can listen to the port. Listening to a known port can be either anonymous or subscription based. In anonymous mode, broadcasting application continuously transmits on a known port and any application can listen to the port. In subscription based mode, the broadcasting application will not transmit until there is at least one recipient, interested application, which will have to request for service and disconnect when done using the service.

Virtual ports can be implemented by enabling a handshake between participating modules/applications. Applications providing the service generally open a port and connect to the port. For every accepted connection request, CID is generated by the service provider and is passed back to requesting entity in an acknowledgement. Subsequent communication is performed using this CID. In general, the CID is unique to the entity that generated it. A disconnection message is used to stop communication and the CID is then returned to the pool, for example to be reused later. If the service provider runs out of CIDs, it may return a NAK to incoming connection requests with appropriate NAK ID. In case of communication failure, for example module shut down, too much waiting time, too many retries, etc., after waiting for sufficient retries to send a message, one or more embodiments may assume that the communication has stopped and CID is then returned to pool. As the CID are generated by the service provider and are unique within the entity, there can be duplicate CIDs on other sub-entities. To avoid the conflict because of duplicate CIDs, two CID tables may be maintained, one for the CID generated by the system, and the other for the CIDs generated by other systems engaged in communication. The creator of CID sets the "CID Source" flag, hence when other involved applications look at this flag, they perform lookup in appropriate CID table. Each entity may therefor maintain a table shared by the applications running on it. This table is maintained at the session layer and serves as a reference table for routing incoming data packets to respective ports/sockets.

As example scenario is illustrated in the following table, and is also shown in the bottom portion of FIG. 10A for illustration purposes and is not intended to limit the invention as claimed. As shown, the connection type may be set to a value indicative of a connection-oriented type of communication, such as TCP as shown, or a connectionless communication type, such as UDP as shown, or a "Service", for example an application that exists to log data for other applications. The destination address, destination port and communication ID generally uniquely identify a row in above-mentioned table. Destination address is the logical address of a device engaged in a communication. Embodiments may support repeated entries with the same destination address, which indicates multiple active connections with the same destination device. The source port field stores the local port number responsible for handling communication(s) with the CID associated therewith. Depending on CID, received messages are routed to the respective port. Multiple repeated entries in the source port column suggest various applications communicating over same port, which may be indicative of one-to-many communication for example. In one or more embodiments, applications may register or otherwise provide a request to a service provider to receive messages. The destination port is the port number on the destination device engaged in a communication. The communication between a destination port and the local port associated therewith takes place over the respective CID. Hence, CID behaves as a key for this communication. Since the CID is a unique number assigned to distinct communication requests, and which may be implemented with a particular data type of a certain size, there may be an upper limit to the number of active connections that can be handled by the system/application. The upper limit is thus an upper numerical limit of the CID. Once the count of unique CID's exceeds the upper limit, one or more embodiments send a NAK to new incoming connection requests. The File Descriptor (FD) functions similar to file handler or file descriptor in standard operating systems as one skilled in the art will recognize. Communication related operations are performed using this descriptor. Repeating entries of FD suggests multiple connections are being served by one application, many-to-one type of communication. See also FIGS. 10B-D for specific message structures utilized in one or more embodiments of the invention.

| Connection Type | Destination Address | Destination Port | Source Port | CID | File Descriptor |
|---|---|---|---|---|---|
| Service | 8 | 50 | 40 | 100 | 55 |
| TCP | 5 | 23 | 60 | 72 | 63 |
| Service | 15 | 68 | 40 | 110 | 87 |
| UDP | 4 | 20 | 55 | 103 | 21 |

The transport layer is another layer in the protocol stack and is responsible for transport layer to transport layer delivery of data. This layer handles flow control, timeouts, acknowledgements and fragmentation and reassembly of data and also resolves the data priority. At least one embodiment of the protocol stack supports two or more priority levels, for example three priority levels, High priority, Medium priority and Low priority and depending on the priority of data, the transport layer puts the data in a respective priority queue. The transport layer may be implemented with two sub-layers namely the transport upper and lower layers. The transport upper layer along with manager and session layers resides in application space, whereas the transport lower layer along with data link layer resides in kernel space. The transport upper layer handles reading and writing to priority queues, fragmentation and reassembly of data and transport-to-transport layer acknowledgements, whereas the transport lower layer may be implemented as a very thin layer and handles reading from priority queues and communication with one or more other stack layers, for example a lower stack layer. This structure along with an exemplary message types in FIGS. 11A-B.

The transport layer generally ensures that manageable sized datagrams are sent over the underlying bus. Hence, this layer looks at the data coming from upper layers and if the size of data exceeds Maximum Transmission Unit (MTU) size, the layer fragments the incoming data to fit within MTU boundary. Thus, embodiments of the invention may utilize any type of bus of any size, e.g., one bit as per a serial bus, or multiple bits as per a parallel bus of any width. The layer adds appropriate information to the data so that it can be reassembled faithfully at the receiving end. If the incoming data can be sent in three fragments, 'Fragment ID' field is used to number the fragments starting from '1' and the 'Extended flag' bit is not used. All zeros in the 'Fragment ID' field indicates an un-fragmented message and hence is treated as a standalone message. If a message requires more than three fragments to be transmitted, 'Extended Flag' is set, which enables an extra of 8 bits (Extended Fragment ID field is 8 bits) to be used for numbering the fragments. With this flag set, there are total of 10 bits available for numbering which can support 1023 ($2^{10}-1$) fragments. At the receiving end, 'Extended flag' is inspected to determine if 'Extended Fragment ID' is used or not. If the flag is set, the receiver assumes the fragments to arrive in sequence, starting from sequence number 1. But, if the flag is not set, the receiver inspects the 'Fragment ID' field. If the 'Fragment ID' field has zero in it, it indicates an independent message, but if it's a non-zero value, the receiver treats the received message as fragmented data (expects a maximum of three packets). Once all of the fragments are received, the receiver will re-assemble all the fragments into one message. To do this, the receiver aligns all the received messages in ascending order of their fragment ID. Then the receiver verifies that no fragment has been missed in the sequence. If all fragments are received successfully, the receiver removes the 'Transport layer' header information from all the related fragments and concatenates them into one message. If Transport layer has limited memory to re-assemble all the fragments, it forwards the fragments up the stack, as they arrive, which gets reassembled in application buffer.

Congestion control is also provided by the transport layer, which may implement messages dedicated specifically for transport layer to layer communication. These specific messages are consumed at transport layer and not passed up the stack. One such message is the window message, which is exchanged to determine window size for data exchange.

Before sending the first fragment from fragmented data, the transmitter requests a window size from receiver. The receiver looks at the available buffer space in the application buffer and computes the number of fragments it can stage before running out of available memory. It responds to transmitters request with this computed number as window size. Then the transmitter sends window size worth of fragments before expecting an acknowledgement. Once the receiver receives all the messages transmitted in a window, it verifies that all the fragments are in desired sequence and sends acknowledgement for last received fragment in the sequence. If the receiver determines that fragment(s) is missing, it sends an NAK for the missing fragment and the transmitter re-transmits the respective fragment(s). The transmitter may check for window size in middle of communication to keep the data exchange optimized, also, if the receiver gets low on resources, it can explicitly send a window response and update the transmitter about the window size.

The transport layer is also responsible for the reliable delivery of data. The transport layer has ability to ensure delivery of data to the receiving end. Transport layer has a field for acknowledgement. The receiver may send an acknowledgement for every received data packet with the acknowledgement flag set. In case of fragmented messages, an acknowledgement is sent when the last fragment in a window has been received or last frame in the message has been received or timer expires before all messages have been received.

Embodiments of the transport layer may also implement a "time to live". For example, after transmitting a message, the transmitter initiates a timer and waits for an acknowledgement. If acknowledgement is received, the timer is reset and next packets are transmitted. But if no acknowledgement is received, the transport layer re-transmits the message and again waits for an acknowledgement. The transmitter will retry to send the message certain number of times and if it fails to get an acknowledgement, it will assume that the receiver is not available and will inform upper layers. In case of fragmentation, the transmitter sends window-sized messages and then waits for an acknowledgement on the last fragment sent. If the timer expires, the transmitter will resend the messages again.

The transport layer also may implement fault detection and recovery. For example, the transport layer at the receiver may request the transmitter to re-transmit selected frames through layer-to-layer messages.

The transport layer may also implement priority for messages. For example, the upper layers may pass the message priority down to this layer and this layer adds the priority to the message header. Header has a two bit fields for message priority and hence there are four priority levels possible in one or more embodiments although any number of bits may be used for priority to implement more levels and this applies to all message partitions and bit numbers described herein. Each priority level has its own queue and depending on message priority, transport layer puts them into respective queues to be processed by other layers. As there are four priority levels in a 2-bit embodiment, there may be a maximum of four priority queues and a minimum of one queue, but the number of priority queue depends on the number of priority levels used.

The data link layer is another layer, by way of example and not limitation the bottommost layer, in the communication stack and is responsible for subsystem-to-subsystem delivery of data. This layer completely resides in the kernel space. Data link layer may also be implemented with two sub-layers, for example a Link Layer and Media Access (MAC) layer. The link layer verifies data integrity by calculating/verifying CRC for each outgoing/incoming data frame and also handles any hardware acknowledgements for example. The layer also handles requests for unique logical addresses as well and generates and assigns unique addresses. The MAC layer utilizes driver(s) handling the underlying physical communication channels or bus(es). As the data frames arrive on the buses, the MAC layer copies the received data into a memory pool and passes the pointer to the copied data to Link layer. At least one embodiment supports communication over multiple underlying data transfer technologies or hardware implementations such as serial, CAN, SPI, SDIO, USB, or any other type of communications medium or data bus. This structure along with an exemplary message types in FIGS. 12A-B.

In one or more embodiments, the data link layer is responsible for data integrity, for example through the use of CRC checking or any other type data integrity coding or format desired. Embodiments of the data link layer are also responsible for logical address assignment. For example, this layer is responsible for assigning and managing logical addresses of modules in a device. All the modules like Pump Motor Controller, Power Supply Controller, Communication Engine, User Interface Controller, etc., have a unique ID so that they can be uniquely identified in a pump. The protocol stack can support 254 modules as the address field is 1 Byte field and logical addresses 00, 01, and FF are reserved addresses. If modules are identified according to their unique hardware address (MAC addresses), and as the hardware addresses are more than a Byte in size, this would add overhead to the protocol. To avoid this, each module may be assigned a logical address between 1 to 255 and this layer then maintains the assigned addresses. The application layer does not need to know what the hardware address is or what the logical address is in general, which simplifies logical and API calls.

One of the modules is generally assigned with the task of generating unique logical addresses for other modules in the device, no matter if those modules are connected directly to this special module or not. When the device powers on, all the modules power on as programmed. The module responsible for generating address for devices is called the "root" device. The root device is aware of its special role and assigns itself a logical address of 01. As other modules wake up, they assume their logical address as 00. They know that 00 is not a valid address but also know that there exists a module with address 01 who can provide a unique address to them.

Hence, these modules send address requests to a destination with address 01. On receipt of this message, the root module checks its internal table to verify if the requesting hardware already has a logical address assigned. If a logical address is assigned, the root module sends that same logical address in response; else it generates a unique logical address, updates this address in its internal table against the requester's MAC address and sends this address in response. On receipt of an Address Response, the requester module starts communicating with this logical address.

A module in one or more embodiments may not communicate without a valid logical address. If multiple modules try to request for a logical address, there will be collisions. Due to collisions, no requests ever reach the root module, and thus none of the modules receives a logical address. In this scenario, other modules will retry after a random period of time. Depending on the criticality of device, the amount of random time can be varied, i.e. critical devices may wait for lesser period of time before a retry. The amount of wait time may be part of configuration and the devices may wait with reference to their internal clock for example.

If a device does not desire to use the dynamic addressing mechanism, each module may be programmed with a unique address, for example to implement a static versus dynamic address assignment scheme. Embodiments may still utilize a root module that maintains the addresses of the connected modules.

Embodiments of the data link layer may also implement routing. As mentioned, a module may have multiple bus types or topologies and there may be different type of devices connected on various buses. If a Data Link layer receives a packet that is not addressed to it, it first checks if it has multiple bus architectures and if true, it forwards the message to other buses; else it simply discards the packet. This kind of addressing mechanism is well suited for star topology for example. Hence if PMC1 wants to send data to PMC2 but there is no direct data path, then it will re-route it through the root module. In this case, the root module can broadcast the message in the network or perform a lookup in its internal table and just forward the packet on a specific line. Hence, in one or more embodiments that implement routing, each module that supports multiple communication buses may maintain a list of all devices directly connected to the module so that they can efficiently route the packets. As stack supports data routing, it seamlessly bridges multiple heterogeneous data buses, thus making communication, bus topology independent. Few examples of possible bus topologies include Ring, Star, Mesh, and Tree topologies or any other topology that may be utilized to transfer data.

Figure 3:
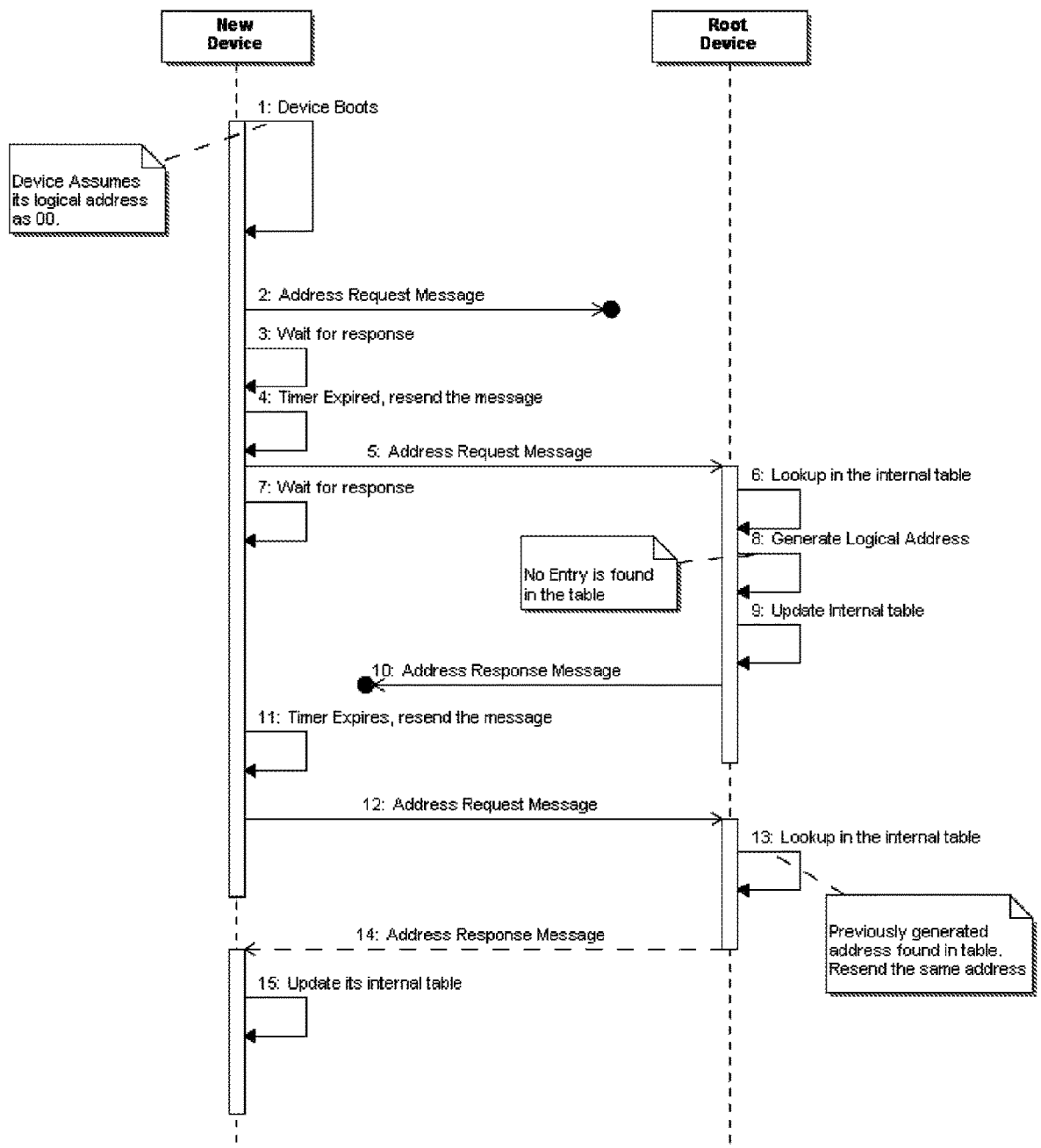
FIG. 3 illustrates an embodiment of an address request method implemented within the manager layer.

FIG. 3 illustrates an embodiment of an address request method implemented within the manager layer. As shown, when a device is added to the system, for example hot-swapped in, the device boots and requests an address from the root device. The new device waits for a response and if a timeout occurs, requests an address again. Once the root device receives the address request message, it looks up an available device number and generates a logical address for the new device and updates the table. Alternatively, if there are no available numbers left a NAK with appropriate error message may be returned to the new device. The root device returns the new device logical address to the new device in an address response message. Any further requests for the address are handled by lookup via the root device. The new device stores the logical address in a local table for further use. This capability generally does not exist in medical devices or infusion pumps since the configurations are generally assumed to be fixed, using a fixed operating system and fixed bus without regard to potential new devices and new types of devices that may communicate with a root device.

Figure 4:
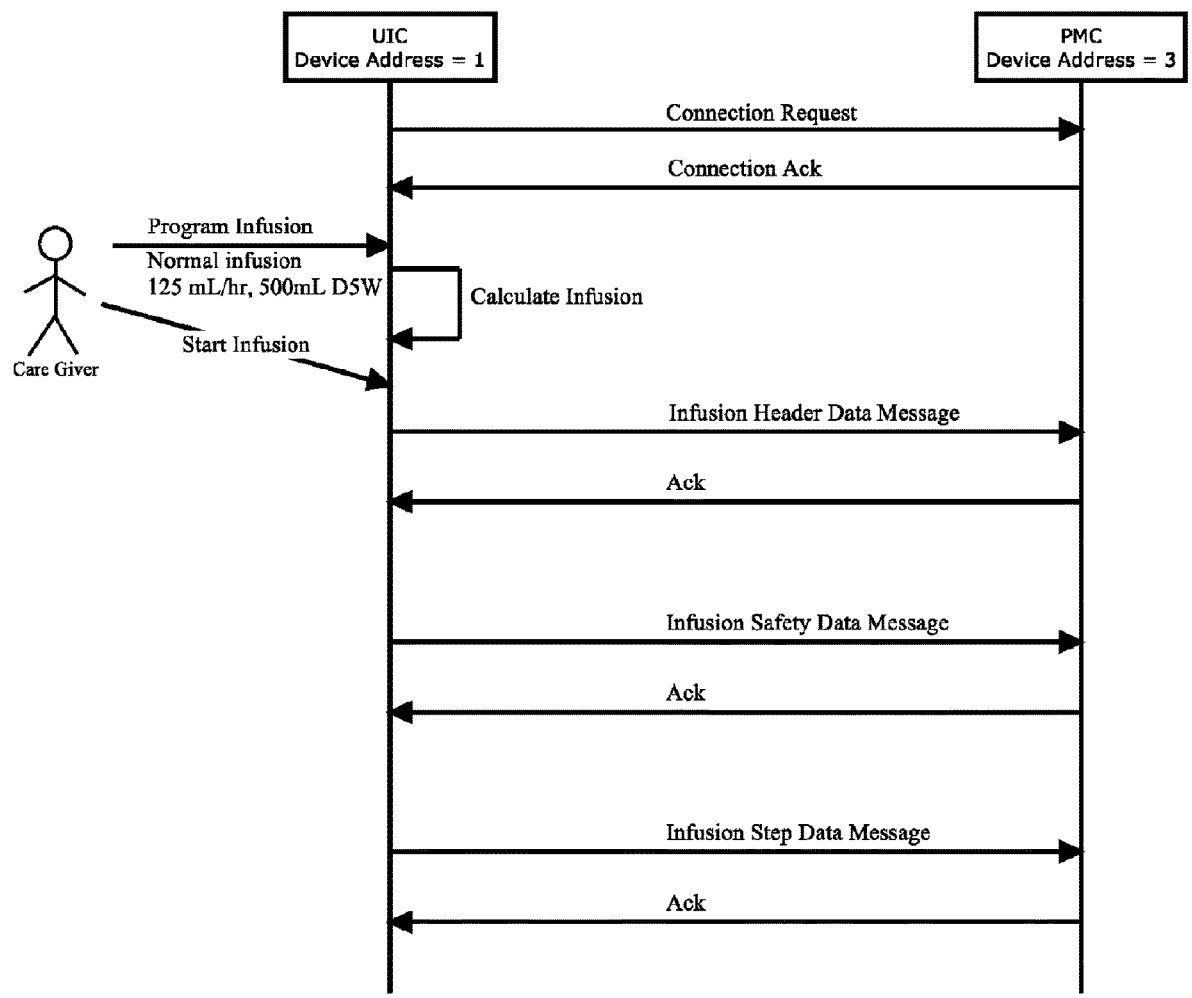
FIG. 4 illustrates an embodiment of a simple infusion sequence utilizing various messages provided by embodiments of the method.

FIG. 4 illustrates an embodiment of a simple infusion sequence utilizing various messages provided by embodiments of the method. Once the address of a new device is obtained, it may communicate with the other components within the system. The figure shows user interface controller UIC having device number 1, initially connecting to a drug infusion pump having device number 3, wherein the logical addresses of the devices, or device numbers are obtained as shown in FIG. 3. The UIC accepts input from a Care Giver that indicates an infusion is to take place. The UIC application calculates the necessary steps to achieve the infusion and sends an infusion header and data message to the drug infusion pump, which acknowledges the message. The UIC then sends an infusion safety data message, which is acknowledged and after the infusion is complete, the UIC sends an infusion stop data message, which is acknowledged. This scenario is a typical scenario that enables any type of drug infusion pump to be added to a system and utilized, for example in a hot swap scenario where an infusion pump may return an error or a different type of drug infusion pump is to be added to the system and utilized for example.

Figure 5:
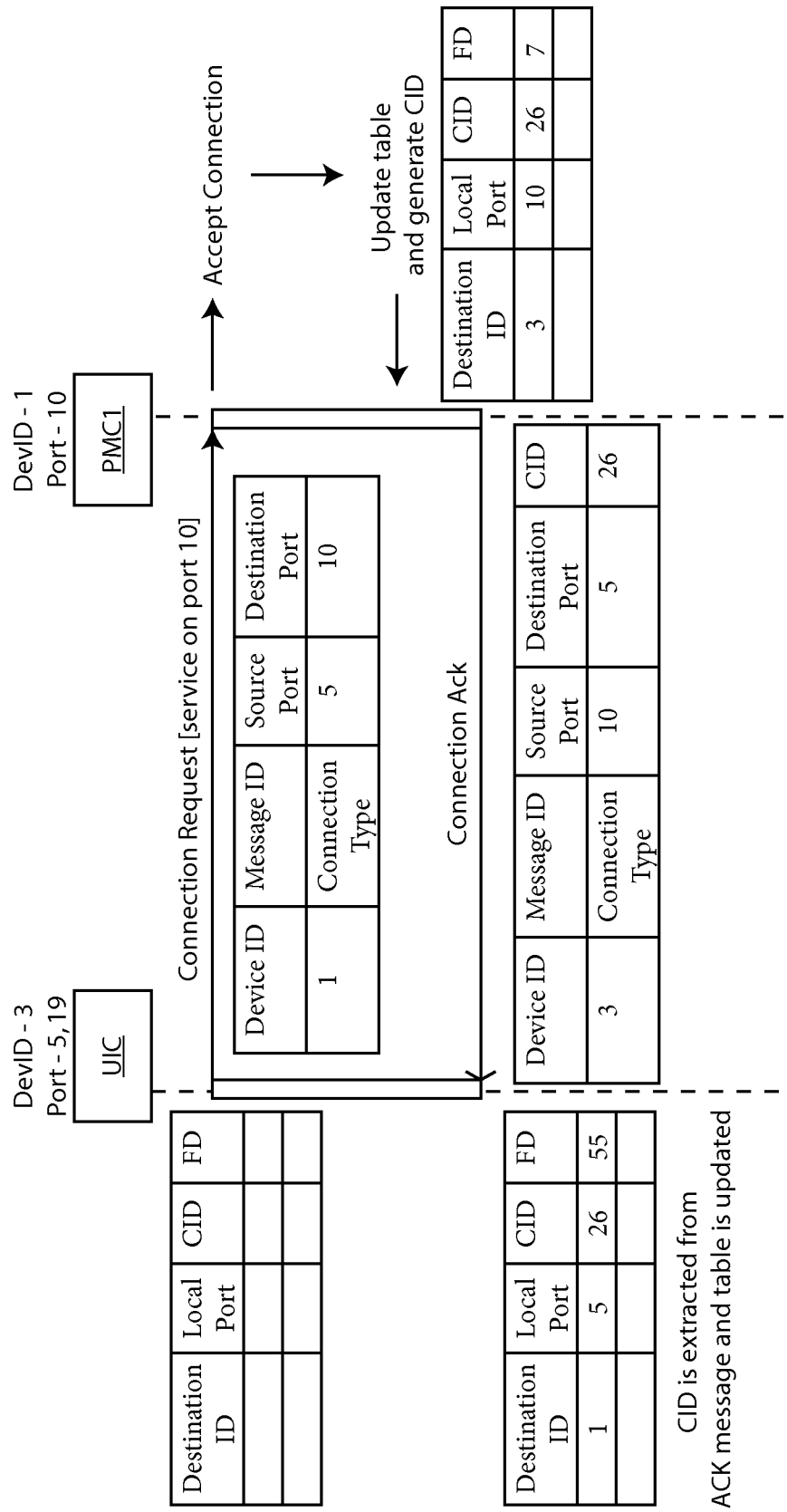
FIG. 5 illustrates an embodiment of a connection method implemented within the session layer.

FIG. 5 illustrates an embodiment of a connection method implemented within the session layer. In the scenario shown, the UIC requests a connection in order to communicate with the PMC to command the PMC and/or for example obtain status updates. In this case, PMC acts as a service provider as the PMC is providing status updates on a known port. UIC sends a connection request to PMC on that port, e.g., port 10, shown as a message passing from left to right. After receipt of the connection request, the PMC accepts the request, generates a unique CID, e.g., 26 for this communication and updates its internal table. The PMC sends the generated CID back to UIC as a part of connection accept message, shown traveling from right to left. On receipt of connection accept message from the PMC, the UIC extracts the CID from the message and updates its internal CID table as shown in the lower left. The UIC then sends an acknowledgement message to the PMC to confirm the successful receipt of CID. If the PMC is not able to process the request from UIC and hence cannot establish communication, the PMC sends a connection reject message to the UIC. On receipt of connection reject message, the UIC may retry to obtain a connection. See also FIGS. 10A-D, 11A-B and 12A-B for an embodiment of the exemplary message structures that may be utilized to form an implementation of various layers, which are described further in detail below.

Figure 6:
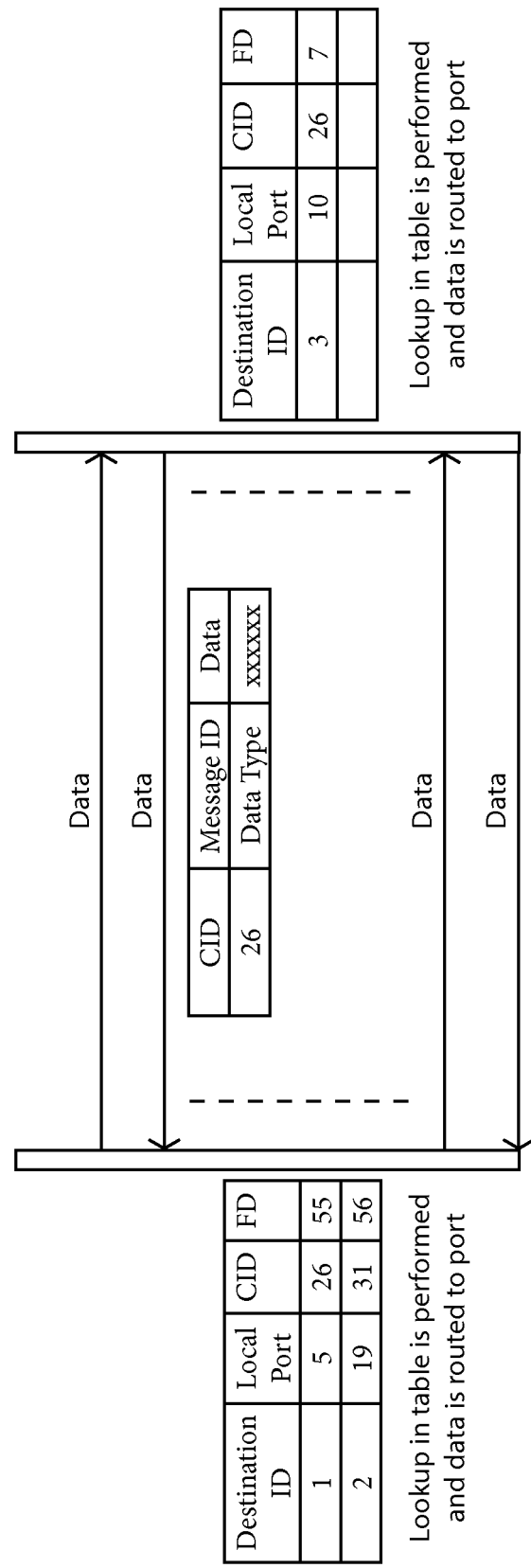
FIG. 6 illustrates an embodiment of a data exchange method implemented within the session layer.

FIG. 6 illustrates an embodiment of a data exchange method implemented within the session layer. Once the PMC receives acknowledgement from the UIC, the connection process is complete. At this time, both devices may exchange data using the agreed CID. When the session layer of PMC receives any data from the UIC with a valid CID, it performs a lookup in its internal table against the 'Destination ID' and 'CID' to resolve the port number where the packet is to be forwarded.

Figure 7:
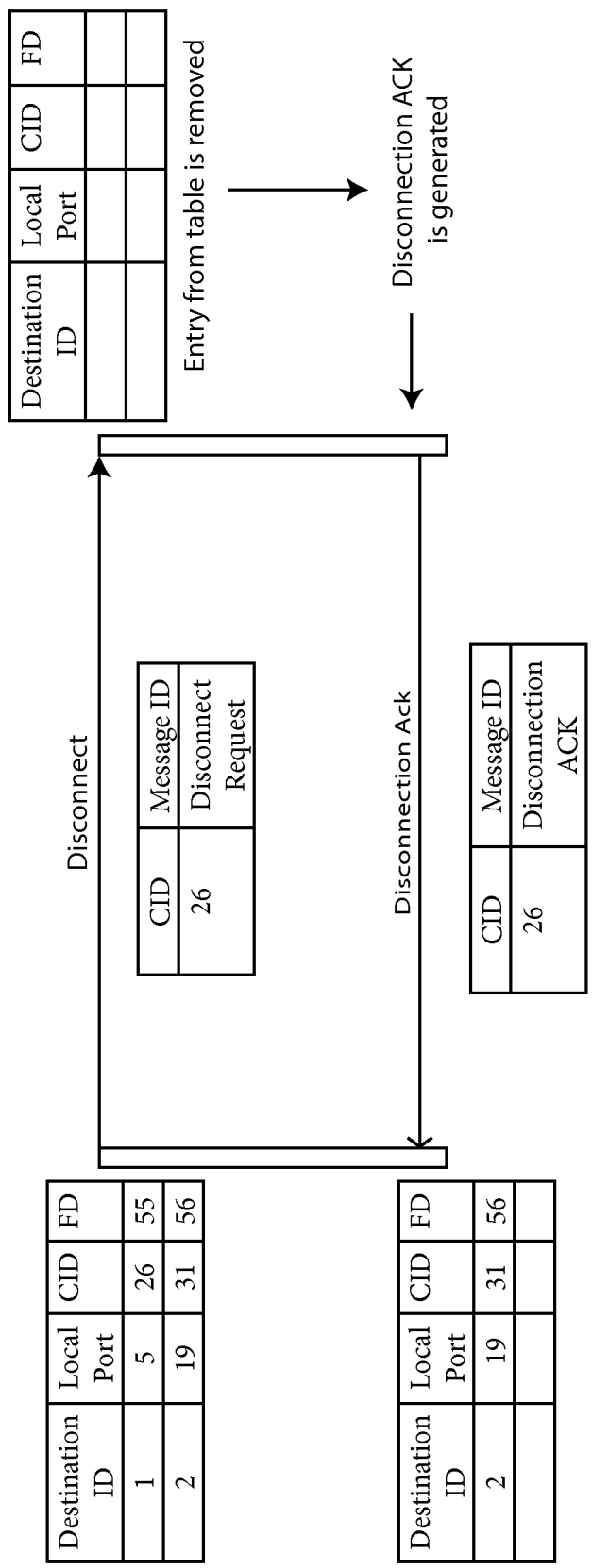
FIG. 7 illustrates an embodiment of a disconnection request method implemented within the session layer.

FIG. 7 illustrates an embodiment of a disconnection request method implemented within the session layer. On completion of data transmission, either of the communicating parties may request for a connection termination. As shown, the UIC initiates the process of connection termination. It sends a disconnect request to PMC with the respective CID. The PMC processes the request and if there is no active communication, the PMC will send an acknowledgement to the UIC and delete the CID entry from its table. On receipt of disconnection acknowledgement from PMC, the UIC also removes the CID entries from its table.

Although the general session layer communication protocol has been described above, a more in-depth description of the Session layer messages follows, according to one or more embodiments of the invention. The message structures utilized in one or more embodiments of the invention as described below are shown in FIGS. 10B-D.

Connection Request Message

For a connection-oriented communication session, when an application opens a socket to communicate over a port on some other device, a handshake is performed before the communication starts. The handshake begins with a connection request type message to the service provider. The "layer flag" is set for this message type. Therefore, the request packet is consumed by the session layer. The connection type may be initially set to "Unknown" suggesting that the data packet is neither connection-oriented nor connection-less. The message type is set to "Connection" as the command is used to establish new connection. The message is a request for establishing new connection; hence "Command" field has "Connection Request" set. The application requesting a connection specifies the destination's port address and also provides its own port address, hence the connection request packet has source and destination port address.

Connect Accept Message

On receipt of a connection request message, if the service provider has enough resource, it responds with a connection accept type of message. The service provider generates a CID for the communication and sends it to the requester as a part of this message. As the connection requesting entity has no information of the generated CID, the service provider sends source and destination port address as a part of this message to let the other end know about the generated CID.

Connection Acknowledgement Message

On receipt of a connection accept message, the requesting end updates its internal table with the received CID. In response to connection accept message, the requesting end sends an acknowledgement message to indicate the service provider about the receipt of CID and complete the handshake. It is possible that multiple applications on one module request to communicate with one application on another module on the same port number, e.g., many-to-one. To inform the service provider about the particular application that is sending an acknowledgement, "source port" is added to the acknowledgement message.

Connection Disconnect Message

Once the communication is completed, any one of the participating entities may request a connection disconnect for a graceful termination of the connection.

Connection Disconnect Acknowledgement Message

This message is sent as an acknowledgement on receipt of a disconnect message. The message is intended to ensure that a communication is not terminated if an active connection still exists. If a disconnection acknowledgement is not received within a certain time period, a disconnection attempt may be made again.

Connection Reject Message

If the service provider cannot accept any new connections, it sends a connection reject in response to a connection request message. In the connection reject message, it sends the reason for rejecting the request. On receipt of a connection reject message, the requester may retry after some time for example.

CID Info Request Message

Any participant involved in communication can request for status of CID. This message acts as a ping message to verify if the destination port is open and CID is an active CID.

CID Info Response Message

On receipt of a CID Info request, a CID Info Response is transmitted. This message contains the source and destination port addresses involved in communication, window size for transmission, etc., and also indicates if the CID is active or not.

Socket Status Request Message

This message is utilized to request socket related information such as the type of socket, purpose of opening this socket, etc.

Socket Status Response Message

This message is sent in response to Socket Status Request message. The message contains socket related information such as the type of socket, purpose of opening this socket etc.

Subscribe to Service Message

The communication protocol enables applications to provide a service, e.g. a broadcast service. For example, the PMC may have a service running that broadcasts PMC status periodically on a known port. If the UIC requests the PMC status, it may simply subscribe to this service with the PMC and receive the messages. Typically these services are one-way communication.

Subscribe to Service Acknowledgement Message

Once the service provider receives a subscription request, it has to provide a CID to the requester. The CID is delivered through an acknowledgement message.

Unsubscribe from Service Message

If a subscribed application no longer desires to be subscribed to a service, it may request to unsubscribe. On receipt of an unsubscribe service message, the service provider removes the entries from its internal CID table and sends an acknowledgement to the requester. If the service provider finds that there is no one subscribed to a service, it may decide to stop the broadcast service until it has at least one subscribed application.

Unsubscribe from Service Acknowledgement Message

On receipt of this message the application requesting to unsubscribe, removes entries of CID from its internal table and releases the involved sockets and ports.

Device Address Request Message

An application may request a logical address for a device using this message.

Device Address Response Message

On receipt of an "Address Request" message, a device sends its address as a part of the response message. Alternatively, a Device Address Response Message may be sent independently at anytime and may not necessarily be tied to a request message.

Device Type Request Message

This message is used to request name of a device. Every connected device has a unique address but may have non-unique names or no names. Device types can be PMC, CE, UIC, etc.

Device Type Response

This message is generally sent in response to "Device Type Request" message and contains the type of the device sending this message. Alternatively, a Device Type Response Message may be sent independently at anytime and may not necessarily be tied to a request message.

Connection-Oriented Data Message

At least one embodiment of the session layer adds just two bytes of header information when sending data between devices. The CID is generated and exchanged during the handshake process prior to data transfer.

Connectionless Data Message

Connectionless data transfer is used when no handshake is required to transfer data. As there is no handshake, there is no CID generated for the communication and hence both source and destination port numbers are utilized to ensure the delivery of data.

FIGS. 11A-B and 12A-B illustrate corresponding message structures for exemplary embodiments of the Transport layer and Data Link layer respectively and are described further below.

Figure 8:
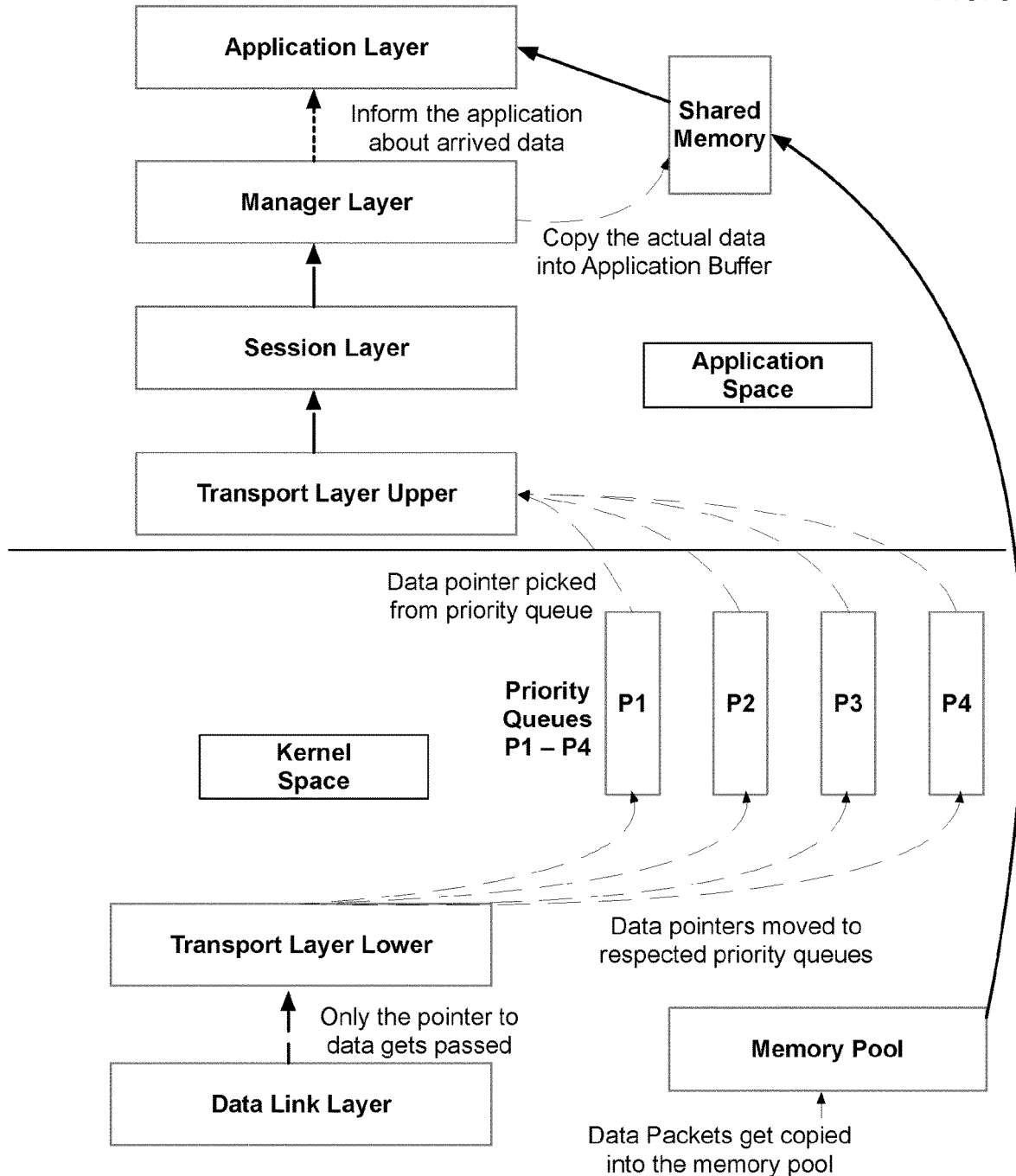
FIG. 8 illustrates a layer flow diagram that shows the flow of data within the various layers implemented in at least one embodiment of the invention.

FIG. 8 illustrates a layer flow diagram that shows the flow of data within the various layers implemented in at least one embodiment of the invention. Specifically, data flow up the protocol stack for incoming data is shown. The destination application buffer location is not known until the data frame moves up to manager layer. Hence, the fragment is stored in a memory pool until it reaches manager layer and once the target application is resolved, the data is copied from the memory pool into application buffer. In one or more embodiments, memory utilization may be minimized by returning a buffer to memory if the buffer is over a predefined age threshold.

Data Link Layer

Data Link layer controls one or more physical communications links, data buses. The layer filters the messages directed to the specific device and ignores other messages. The layer may compute a CRC on the received packet and verify it with the received CRC. Valid data frames are copied into a memory pool and pointer to these messages are forwarded to the transport layer.

The transport lower layer and data link layer run as an independent service and stores data in the designated priority queue, P1, P2, P3 or P4. The transport upper layer, session and manager layers execute in the application space, and the transport upper layer maintains pointers to the priority queues and Communication ID tables. In one or more embodiments, the memory pool, priority queues and CID tables are in shared memory space.

In one or more embodiments, the data link layer is further divided into two sub-layers, a link layer and a MAC layer. The MAC layer may interface with bus drivers and has a buffer for each underlying bus. As the data arrives on these buses, the data is copied into these buffers and then forwarded to link layer. The buffer may be implemented as a pair of buffers, while one buffer is used for receiving new data, other buffer is used to transfer previously received data.

The link layer copies the data from buffers into the memory pool. The memory pool is a contiguous memory block and each memory block may be implemented as a factor of frame length. As the application consumes data, the data is removed from the memory pool to make room for new data packets. As the application consumes data randomly, there may be memory holes in the memory pool. Hence, the link layer generally maintains a list of available memory locations in the memory pool. When memory is freed from the memory pool, the pointer to available location is added at the end of this list. When a new packet arrives, it is placed at the memory pointed by the first element in this list. If there is no element in the list, memory pool will be considered full and the packets will be dropped. In one or more embodiments of the invention a memory manager may be utilized to control access to memory from the various layers, including concurrent access control of memory from the various layers. Embodiments of the invention may minimize or altogether avoid multiple copying operations by maintaining one copy of data in the memory pool while passing pointers to the memory as the data moves up and down the stack. By controlling access to the memory during access, semaphores may be utilized to ensure data integrity while allowing multiple processes to effectively utilize the data in a concurrent manner. Avoiding multiple copy operations enables minimal memory utilization in embedded environments and minimizes processor utilization as well.

As the transmitter has tendencies to push data on buses, they can soon over-utilize the bus by transmitting too much data. The bus driver at the MAC layer in one or more embodiments may be implemented to handle such scenarios.

Transport Layer

In one or more embodiments, the transport layer may be divided into two sub-layers, a transport upper and a transport lower layer. The transport upper layer resides in application space whereas the transport lower layer resides in kernel space. These two layers together handle transport layer functionalities.

The transport layer is implemented in one or more embodiments to reassemble fragmented data and also to resolve data priority. When a new data packet is received by transport lower layer, a timer may be started for the data. If the data is not consumed before the timer expires, the data may be discarded and the memory freed from the memory pool. This avoids memory starvation if no application exists to consume received data. If the acknowledgement field was set, the transport layer sends a NAK, "timed out in priority queue" error code, for example.

The transport layer header has an acknowledgement flag and if the flag is set, the receiving transport layer will have to send some kind of acknowledgement for the received data fragment. If fragmented data is received, the acknowledgement is sent after receiving window size amount of data or a complete message. This flag is set for a connection-oriented data transfer to ensure delivery of data. This flag may also be set in a connectionless data transfer only if data fragmentation is utilized.

Fragmented Data Packet Handling

In case of fragmented data, before the transmitter starts sending any data fragments, the transport upper layer at the transmitter first requests a window size from the receiver. The window size may be exchanged once during first data transfer or may be obtained before every data transfer. Window size is the number of data fragments that can be sent before an acknowledgement can be expected. When receiver receives a window size request, transport upper layer at receivers end, computes the amount of free memory in application buffer and sends the response as window size in the 'window size response' message.

In one or more embodiments, the transport upper layer at the transmitter side initializes a data structure for the CID that requested a window size. In this structure, the transport layer stores the CID, last reported window size, last successfully received fragment number and the maximum allowed time period between two fragments, etc. Also, the transport upper layer at the receiver maintains same structure. The transport layer expects that the fragments will be sequentially numbered starting from 1 in one or more embodiments.

As the transmitter receives a window message, it calculates the number of fragments to be transmitted before expecting an acknowledgement. The transmitter starts sending data fragments in sequence starting from fragment number 1 for example.

When the receiver receives first fragment, the transport lower layer starts a timer on the received data frame and places the fragment it into the respective priority queue. The transport upper layer updates the structure and stores the sequence number of the fragment. If the fragment is delivered to the application buffer by upper layers, the upper layers inform the transport upper layer about the success. The transport upper layer updates its structure with the first fragment being delivered. Upper layers do not inform application about the available fragment until all the fragments constituting to a message are received. An application buffer is used for re-assembly of fragments to minimize memory footprint.

If the transport upper layer receives all the fragments for a window successfully, it waits for all the fragments to be delivered to application buffer successfully. Once all the fragments are sent to application buffer, the received fragment number and delivered fragment number match and the transport upper layer sends an acknowledgement for the last fragment in the sequence. The transmitter receives the acknowledgement at the transport upper layer.

Ideally, the transport layer accumulates all fragments, verifies that they are in sequence and merges them into one complete message before sending it up the stack. However, in one or more embodiments, the transport upper layer forwards the frames to the session layer as they are received, but ensures that the fragments are delivered in sequence. This optional implementation may be utilized to lower memory utilization. This is the case since the message does not have to be reconstructed in full within the stack until the full message is received in the application. As the fragment number in the transport header is 10 bits wide in one or more embodiments, the layer can support a maximum of 1023 fragments (fragment number 0 is reserved and represents a non fragment data frame) before the fragment numbering overflow. As each fragment has a maximum of 248 Bytes payload, hence a total of 253,704 Bytes is required at the receiver end for each active connection to accommodate all the fragments. Any other size of fragment number field may be utilized to increase the overall size as one skilled in the art will recognize.

At the receiver, as the fragments are received, transport upper layer updates the last fragment number in its structure. Before updating, it verifies that the received fragment is in sequence with previously received fragment. If it detects a missing fragment, the layer still forwards the fragments up the stack, but in their respective token puts an offset value. Metadata along with a pointer to the received data fragment is called a token. This offset value is used by manager layer to provide a gap while accommodating other fragments around the missing one, so that the gap can be filled once the missing fragment is received. For example to create an empty space in memory so that when the missing frame is finally received, it will be accommodated in this empty space to complete the final message. Meanwhile, transport upper layer waits for the fragments to arrive and then looks for any missing fragment in the sequence. Once the layer generates a list of all missing fragments, it requests for retransmission of fragments from the transmitter. Once the missing fragments are received, they are forwarded to upper layers so that they can be used for filling the empty spaces in final message.

When retransmission is required, transport upper layer at receiver end, sends retransmission request message with the desired fragment number in it. The receiving end maintains a list of missing fragments and as the missing fragments are received, their entry is removed from this list.

If the transmitter retransmits an already transmitted fragment, the receiver compares the fragment number with last received fragment number and will detect that there has been a retransmission. The layer checks if the retransmission was requested by the receiver explicitly or not. If the retransmission was intentional, the fragment is consumed else the fragment is dropped assuming a false retransmission of data.

Once the transmitter sends one window size worth of fragments, it starts a timer and waits for an acknowledgement on the last fragment in the sequence. The transmitter may send any further fragments only when it receives an acknowledgement. If the acknowledgement is delayed and the timer expires, the transmitter may send a "window size" request message before retransmitting the fragments. A receiver may fail to send an acknowledgement if the receiver is too busy or its buffers are full. Hence, a "window size" message is sent because it serves two purposes, the first being that a response to this message implies that the receiver is ready for accepting messages, and the second being that the new responded window size buffer is available at receiver so that chances of getting an acknowledgement increases.

In case of missing fragments, the receiver sends a retransmission request instead of an acknowledgement. A retransmission request can only be sent if the last fragment in the sequence was either received successfully or was found missing. Hence, the transmitter considers a retransmission request message as an implied acknowledgement and no more waits for an explicit acknowledgement, but may wait on acknowledgement for retransmitted fragment.

Missing fragments can be of three types, the first fragment missing, any fragment(s) missing between first and the last fragment of a complete message, and the last fragment itself missing. If the first fragment is missing and the receiver starts receiving from fragment number 2, it accumulates all the messages till it receives window size messages and explicitly requests for the 1st fragment. The same technique is used for requesting any missing fragment between 1st and last fragment.

Missing the last fragment of a complete message may be a complicated scenario because transmitter never informs the receiver about total number of fragments needed to send a message and hence, there is no way for receiver to know when the message completes. Missing "last" fragments can be of two types, missing the last fragment from a window and missing the last fragment of a message. In the case of missing the last fragment from a window, it is easy to detect. Every time a fragment is received, the receiver starts a timer and waits for next fragment to be receive before the timer expires. The transmitter sends the last message for the window and waits for an acknowledgement. If this message is lost, the receiver waits for this last fragment to arrive. The timer at the receiver expires earlier than the timer at the transmitter. As the receiver keeps track of fragment sequences and window size, it realizes that the last fragment was not received on time and hence sends a retransmission request for the last fragment.

A more difficult problem occurs when the last fragment of a message is lost. As the receiver has no idea about how many fragments will constitute a message, it looks for the fragment with 'last fragment' flag set. This fragment indicates the receiver that it was the last fragment from the message. If this fragment is lost, the receiver has no idea when to stop reassembling fragments. To ensure delivery of this last fragment, the transmitter can use following two approaches.

In the first approach, the transmitter knows that the last fragment is approaching. It explicitly reduces the window size to make sure that the last fragment of the message becomes the last fragment of the window as well. As the receiver can detect the last fragment from a window, if the last fragment from a message is lost, the receiver may request retransmission.

In the second approach, the transmitter will send the last fragment with 'last fragment' flag set, followed by few fragments with random payload but with incremental fragment number. If the last fragment of the message is missing, the receiver will detect the missing fragment as there will be gap in sequence numbers and will request for retransmission. When the receiver attempts to arrange the fragments in sequence, it detects the fragment with 'last fragment' flag set and hence discards all fragments following this fragment.

Non-Fragmented Data Packet Handling

For a non-fragmented data frame, it is first received by transport lower layer, which starts a lifetime timer on this frame and puts the frame in appropriate priority queue. The frame is picked from the priority queue by transport upper layer, which forwards it to other layers, for example Session layer.

Session Layer

Session layer major responsibilities are to ensure application-to-application delivery of data and generate unique CID's within a system. The stack works on the principle of service provider and service consumer. The application providing service generates unique CID's for the engaged participants. The CID is unique within the system running the service provider application in one or more embodiments. The CID may be thought of as a key used to hide the information about source and destination ports engaged in communication.

The session layer may be implemented in a lightweight or a very thin layer to a connectionless communication because a connectionless data packet will contain the source and destination port addresses as part of their headers and hence does not utilize a CID.

Packets reaching the session layer may be divided into two categories, namely data and control. Further, the incoming data can be connection-oriented or connectionless and fragmented or non-fragmented.

Connection-Oriented Data Transfer

Connection-oriented data transfer makes use of a connection through a handshake process. After an initial handshake process is complete as is described further below, data exchange occurs. In connection-oriented data transfer, embodiments of the invention utilize a data header with an acknowledgement flag set and connection type set to 01, for example. Data being exchanged may be fragmented or non-fragmented based on the size of the data and the underlying packet size supported by the physical medium.

Fragmented Data

When an application writes to a virtual port, the session layer adds a session layer header to the data and forwards it down the stack. In one or more embodiments, the session layer header is 2 bytes wide. Hence, if fragmentation is needed at the transport layer, the first fragment is set to contain the CID from the session layer while the rest of the fragments may contain only application data. The session layer at the receiving end forwards the first fragment that contains the session layer header, but is unsure as to where to forward other fragments from the sequence as there is no CID information in subsequent headers. Also, if two or more applications on one device want to send data to one device, it is not possible without further information in general at the receiving end to aggregate fragmented data because there is no way to uniquely identify which application is sending what data fragment. To resolve this issue, the transport layer copies session layer header to all the related fragments. As all the fragments will now contain CID, they can be uniquely identified at the receiving end.

The session layer header contains an acknowledgement flag that is utilized in the case of complete messages. As the session layer ensures application-to-application delivery of data, it sets the acknowledgement flag for the receiver to acknowledge successful delivery of data. As the header is copied in each fragment, the session layer will look at the flag and will acknowledge the transmitter every time a fragment is delivered which is not what acknowledgements are generally for, i.e., a complete message acknowledgement.

To avoid this issue, the transport upper layer at the receiver end appends metadata to packets as they are sent up the stack. Metadata along with pointer to received data fragment is called a token and instead of passing data, transport layer passes a token to session layer. In the case of exceptions in behavior of the session layer, metadata provides guidelines for the session layer to follow. For example, the session layer will not send any acknowledgements for data fragments, and when the transport upper layer receives a fragment with a "last fragment" flag set, it updates the metadata so that session layer knows that it needs to send an acknowledgement to the transmitter regarding the receipt of a complete message.

Flow of Control

As the fragments move through the session layer, session layer extracts the CID from the fragments, performs a lookup in the Communication ID table based on CID and the sources logical address obtained from the metadata. The session layer determines the associated file descriptor source and destination ports for the CID. Once the file descriptor is known, it removes all the headers and modifies the metadata to communicate the file descriptor detail to manager layer.

Once the fragment arrives at the manager layer, the manager layer extracts the file descriptor information from metadata and forwards the fragment to respective application. Before the manager layer forwards the message to the application, it determines if the file descriptor is still in use and in the state of accepting data. If conditions are favorable, the message is copied into the application buffer and a "message received" flag in file descriptor is set. If the current operation on the file descriptor is a blocking read, the read function call returns with number of bytes available in application buffer. If the current operation is a non blocking call, the application either checks the flag and if set, reads data from buffer, or the manager layer may make an asynchronous function call on receiving data.

After delivering the data to the application, the manager layer returns the token to session layer. This token contains information about the state of the previously passed message. Depending on the state of token, the session layer performs activities such as sending a session-to-session layer acknowledgement.

If the data is fragmented, session layer further modifies this token and sends it down to transport layer, otherwise the session layer consumes the token. The transport layer determines if the fragments were delivered in sequence they were sent and accordingly controls acknowledgements and window sizes.

Non-Fragmented Data

If a message size is less than the Maximum Transmission Unit (MTU), no fragmentation is required and the complete message is sent in one frame. As the frame moves up the stack, transport upper layer adds very little information to the metadata as complete information for the session layer is already available in the frames header. The session layer reads the header and extracts the data type. If the data type is connection-oriented data, the session layer extracts the CID and performs a lookup in the CID table to determine source and destination ports. The session layer removes all the headers from the datagram, updates the metadata with the destination file descriptor, and forwards it to the manager layer.

Connectionless Data Transfer

As mentioned above, in a connectionless data transfer, the session layer may be implemented in a lightweight or very thin layer. As connectionless data transfer does not utilize a handshake, no CID is generated. Due to the absence of the CID, the protocol header utilizes source and destination port addresses. The session layer reads the destination port address and determines the associated file descriptor and forwards the message to that port. As connectionless data transmission does not guarantee delivery of data, the acknowledgement flag on the frames is set to false.

If a connectionless data frame is larger than the MTU, the transport upper layer fragments the data into manageable sizes without setting the transport layer acknowledgement flag as would be done in connection based communications. During reassembly, if transport layer sees any missing fragments, it discards the complete message. Through a token, the transport layer informs upper layers to discard previously accumulated fragments in application buffer.

Manager Layer

Manager layer handles file descriptors and forwards packets from lower layers to appropriate file handlers. The manager layer also performs the copying of data from the memory pool into the application buffer. The manager layer knows the size of the application buffer and the application buffer size may be smaller than one frame length.

If the application buffer is large enough, the manager layer copies the complete message into application buffer. If the application buffer is not large enough, the manager layer copies data in a sequential manner. The manager layer fills the application buffer with data and waits for the application to read the data before copying the next portion of data. Once data is successfully delivered to the application, depending on the token, the manager layer informs the session layer regarding success.

Control Flow Up the Stack

The flow of control is now described as data moves up the stack from the lowest layer to the application layer.

Data Link Layer

The data link layer control is described with respect to the two sub-layers that make up the data link layer, namely the link layer and the MAC layer. The MAC layer controls the physical bus drivers.

MAC Layer

As the datagram arrives on the physical bus, the bus driver copies the datagram into a buffer. Once the complete datagram is available in the buffer, the MAC layer calls an API in Link Layer to copy the available data into the memory pool.

The link layer API returns a value to indicate the outcome of the copy operation. The operation may succeed or fail. The returned error code provides the reason for any failure. The MAC layer waits for the API to finish the operation before storing newly available data into the buffer.

Link Layer

As discussed in the sections above, the memory pool may be fragmented due to applications consuming data at random rates, resulting in holes in the memory pool. In one or more embodiments, the link layer maintains a link list, or a doubly link list, or bit map or any other data structure capable of storing available memory locations in the memory pool. When a memory location is made available, a pointer to the memory location is added to the tail of the list. When a new datagram is available, it gets copied at the memory pointed by pointer in the head of the list. Though the received message can be of any size and wherein a maximum size exists, for example 256 bytes, the size of the memory pool is selected to be an integral multiple of the maximum datagram size. This simplifies memory management, as the stack is aware of the size of allocated memory given the pointer to that memory. There may be instances when a datagram is available at the time when memory is made available in the memory pool. In this case, both the copy and the delete processes will try to access the list simultaneously leading to concurrency issues. In one or more embodiments, the memory pool may include non-uniform size buffers for a more flexible buffer implementation at the cost of memory management complexity as one skilled in the art will recognize.

When the MAC layer calls an API to copy the data from hardware buffer to memory pool, the API first checks the list for any available memory location in the pool. If memory is available, the API copies the datagram to the memory location pointed by the head of the list and deletes the pointer from the list. If no space is available, for example the link list is empty, or error occurs during the copying to memory pool, the API returns respective error code.

After successfully copying the datagram, the API adds the pointer to the datagram in a list with a number of timer ticks remaining before the data should be delivered to application. This API may be reentrant as the MAC layer may be riding over multiple bus architectures and the data may be available in multiple buffers at the same time resulting in calling this API while the layer is still servicing the previous call.

The protocol stack may be implemented with a time limit within which a datagram is to be used by an application, or else the datagram is dropped from the memory pool. To enable this feature, embodiments may implement a global list containing pointers to each datagram with the timer count on each pointer. As the new packets arrive, an API adds the pointer to this packet at the end of this list. The API adds "time to live" value to the current timer count and generates a timer count that represents an expiration time for the packets. When timer count changes, an API looks at the timer count starting from top most element in the list and starts deleting datagram if their timer counts are less than or equal to current timer count.

Once the data is consumed by the application or the data times out, an API is called to remove the datagram from the memory pool and add the pointer to the available memory list. This API may be reentrant as the data may expire at the same time it was consumed by the application. Both processes may attempt to delete the same datagram, therefore semaphores/locks may be utilized to effectively serialize control.

When data gets copied to memory pool, the link layer generates a token for the packet. The token contains the pointer to the datagram and length of the datagram. This token is forwarded to the transport layer through a transport layer API for further processing.

Transport Layer

After the transport lower layer receives a token, the transport lower layer determines if the frame is a transport-layer-to-transport layer message. If the 'layer flag' is set, then these types of messages are layer-to-layer messages and hence are not forwarded to upper layers. If the flag is not set, transport lower layer looks at the priority of the message and places the token into appropriate priority queue.

In one or more embodiments, the transport upper layer receives the token from the priority queue and determines if the 'extended flag' is set or not. If the flag is set, it indicates that a large volume of data is to be expected and informs the API that an extra byte has been used in header for sequencing large number of fragments.

The layer also reads the "Last Fragment" flag. A set 'last fragment' flag indicates to the layer that the current datagram fragment is the last fragment in the sequence of fragments and hence the end of one message. If there is any fragmentation, at least one fragment will have this flag set.

The layer further reads the acknowledgement flag. If the transmitter requests or otherwise is to be sent an acknowledgement for delivery of the datagram to the receiver's transport layer, the layer will set this flag and the receiver will acknowledge the receipt of the packet. If the devices engaged in communication have agreed on a window size for acknowledgements, then the transport layer acknowledges after receiving window size messages else the layer acknowledges each datagram.

The transport upper layer adds more information to the data token and forwards it to session layer. The transport upper layer informs the session layer if the message is a complete message or not. In case of fragmented message, the transport layer informs the session layer about receiving the last fragment, so that session layer may send an acknowledgement if needed.

Session Layer

From the data pointer in the token, the session layer accesses the frame and extracts session layer header. From the header, session layer first determines if the message is a layer-to-layer message or needs to be forwarded up the stack. If the message is a layer-to-layer type message, then the message is consumed by session layer.

If the layer flag is not set, the frame is forwarded up the stack. The session layer reads the 'Connection Type' field and determines if the message is of unknown connection type or connection-oriented or connectionless. An unknown connection type is generally for the messages exchanged during handshake process, whereas a connectionless message does not need an acknowledgement for delivery, and connection-oriented messages are the ones that use an acknowledgement on successfully delivery.

The session layer further looks into the message type field to determine the type of frame. The frame type is used to determine the purpose of the frame, and only 'Data' type frames are forwarded up the stack and the control type frames are consumed at session layer.

The CID is generated by the application providing a service. Any application that wants to use the service will request a communication ID. CID is unique within one module, for example all of the CID's generated by the UIC are unique within a particular UIC. The CID is generated through a handshake process, where the application using the service sends the details required for uniquely identifying an active connection and receives the CID in response.

The CID specifics and details may be stored in a CID table located in a shared memory region in one or more embodiments, so that the session layers of all the applications may access the CID. In a connectionless data frame, there is no CID information as there is no handshake utilized to establish a connection. Hence connectionless frames contain both source and destination port address in the header.

In a connection-oriented data transfer, there exists a CID in the session layer header. Once the session layer determines the CID from the header, the layer combines the information with the source logical address available in the data token to uniquely identify an entry in CID table. From this table, the session layer determines the source and destination port address and the file descriptors handling the port. The source logical address of the received frame is set by the data link layer along with the file handler information and is forwarded in the data token to the manager layer.

If the received frame is connection-oriented and is a complete message, the session layer maintains a record of the message and forwards the data token to the manager layer. Once the manager layer copies the frame from memory pool into the application buffer, the manager layer notifies the session layer about the successful delivery of data. On receipt of notification, the session layer sends an acknowledgement to the transmitter session layer regarding the successful delivery of data. If the delivery was unsuccessful, as a part of the acknowledgement, the session layer forwards the error message returned from the manager layer to the transmitter.

Manager Layer

The session layer calls an API in manager layer and passes the data token to the manager layer. The manager layer copies the data from memory pool into the application buffer and notifies the session layer regarding the copy. The manager layer notifies the lower layer about the delivery of message by modifying the data token and sending the data token back to the session layer. Once the data is successfully copied, the manager layer removes the frame pointer from the list of frames monitored by the timer and deletes the frame from the memory pool to make room for new packets.

It may happen that the application buffer is smaller in size than the received data frame, in such cases the manager layer will fill the application buffer with what it can hold and wait for the application to consume it. Once the application consumes the message, the remaining portion of the message is copied and the process is repeated until the complete frame is consumed. Before starting the progress of copying messages in small sizes, the manager layer removes the pointer to the frame from the timer-monitored list because the timer may expire and corrupt the message. Also, the manager layer notifies the lower layer regarding successful delivery of data only when a complete message is sent to the application. At the end of the sequential copy process, the manager layer deletes the frame from the memory pool.

In the case of fragmented data, as the fragments are received by this layer, it copies the fragments into the application buffer and notifies the session layer. The session layer forwards the notification to the transport layer. The transport layer, after receiving notifications for a window size number of messages, sends an acknowledgement to the transmitter about receiving the messages. When the last fragment is successfully delivered to the application, it implies that one complete message was delivered. In such cases, the manager layer notifies the session layer of success, and the session layer sends an acknowledgement message to the transmitter regarding the success, thus providing guaranteed delivery of data.

Data Flow Down the Stack

Assuming that in case of a connection-oriented data transfer, the handshake process has already been done and a valid CID has been already generated, the application copies data into an application buffer and passes a pointer to the API exposed by the manager layer for sending data over virtual ports. The application also specifies the file descriptor that handles the communication and the size of data to be written on the virtual port.

The priority of a message is determined by the priority of the virtual port being used or priority can be set for the message passing through. Hence, through a set of API's, the manager layer informs the session layer about the priority of data, size of data, file descriptor for the communication, pointer to application buffer, and if data is connection-oriented or connectionless. If the data is connectionless, the session layer looks into the file descriptor table and determines the port number associated with the file descriptor. The session layer then adds source and destination port addresses as header to the data. If the transfer is to be connection-oriented, the session layer performs a lookup in the CID table and determines CID associated with the file descriptor and adds this CID as header to the data. The session layer then forwards this pointer to the transport layer and waits for an acknowledgement from the receiver.

The transport upper layer determines the size of the data and determines if fragmentation is required or not. If fragmentation is needed, the transport upper layer breaks the data into manageable sizes and adds information to the header so that the data can be reassembled at the receiver's transport upper layer. If fragmentation is not needed, the transport upper layer still adds some information in one or more embodiments. For example, the transport upper layer copies the data from application buffer into transmitter memory pool and depending on the priority of data, stores the pointer into appropriate message queues.

The transport lower layer eventually reads the pointer from the priority queue and forwards it to the link layer. The link layer determines the destination logical address and adds it to the data header, computes a CRC on the frame and adds it to the frame before sending it. The MAC layer determines the bus over which the destination is available and sends the data over that bus.

Flow of Data Up the Stack

As the data frame arrives at the underlying bus, the MAC layer determines if the frame is for the subsystem or for some other subsystem. If it is for some other subsystem, the MAC layer drops the data frame. The MAC layer copies valid data frames into a shared memory region and calls an API in the Link layer to inform it about arrival of new data. Throughout the stack, only the pointer to this data is updated to reduce multiple copying of fragments.

The link layer computes the CRC on the received frame and compares the computed CRC with the CRC on the received frame. Frames with invalid CRC's are dropped. Pointers to valid frames are forwarded to the transport lower layer.

The transport lower layer reads the priority of the frame and adds a pointer to the frame to the respective priority queue. The pointer to the frame remains in the queue and waits for appropriate application to consume it. Eventually, the target application's transport upper layer reads the pointer to the frame from the priority queue.

The transport upper layer looks at the headers to determine if the data is fragmented or a complete message. If the data is fragmented, the layer reassembles all the messages from the sequence and then forwards it to the application layer. If the data is not fragmented, it directly forwards the pointer to the frame to the session layer through appropriate API calls.

The session layer looks at the frame headers and determines if the message is of type connectionless or connection-oriented. If the message is connectionless, the session layer looks at the destination port number and determines the file descriptor handling that port. The session layer forwards the pointer to the manager layer with appropriate file descriptor information. If the frame is connection-oriented, the session layer reads the CID and determines the file handler handling that communication. The session layer then forwards the file descriptor information to the manager layer and waits for an acknowledgement from the manager layer. The manager layer sends an acknowledgement indicating whether the data was delivered to the application or not. This information is used by the session layer to acknowledge receipt of data.

The manager layer may be implemented with a lightweight or thin layer and is responsible for copying the data from the memory pool into the application buffer and freeing the memory pool. Once the data gets copied into the application memory, the manager layer informs the application about data being available. The manager layer sends an acknowledgement to the session layer. Thus, to the applications, the manager layer offers synchronous and asynchronous methods for reading and writing to virtual ports.

Figure 9:
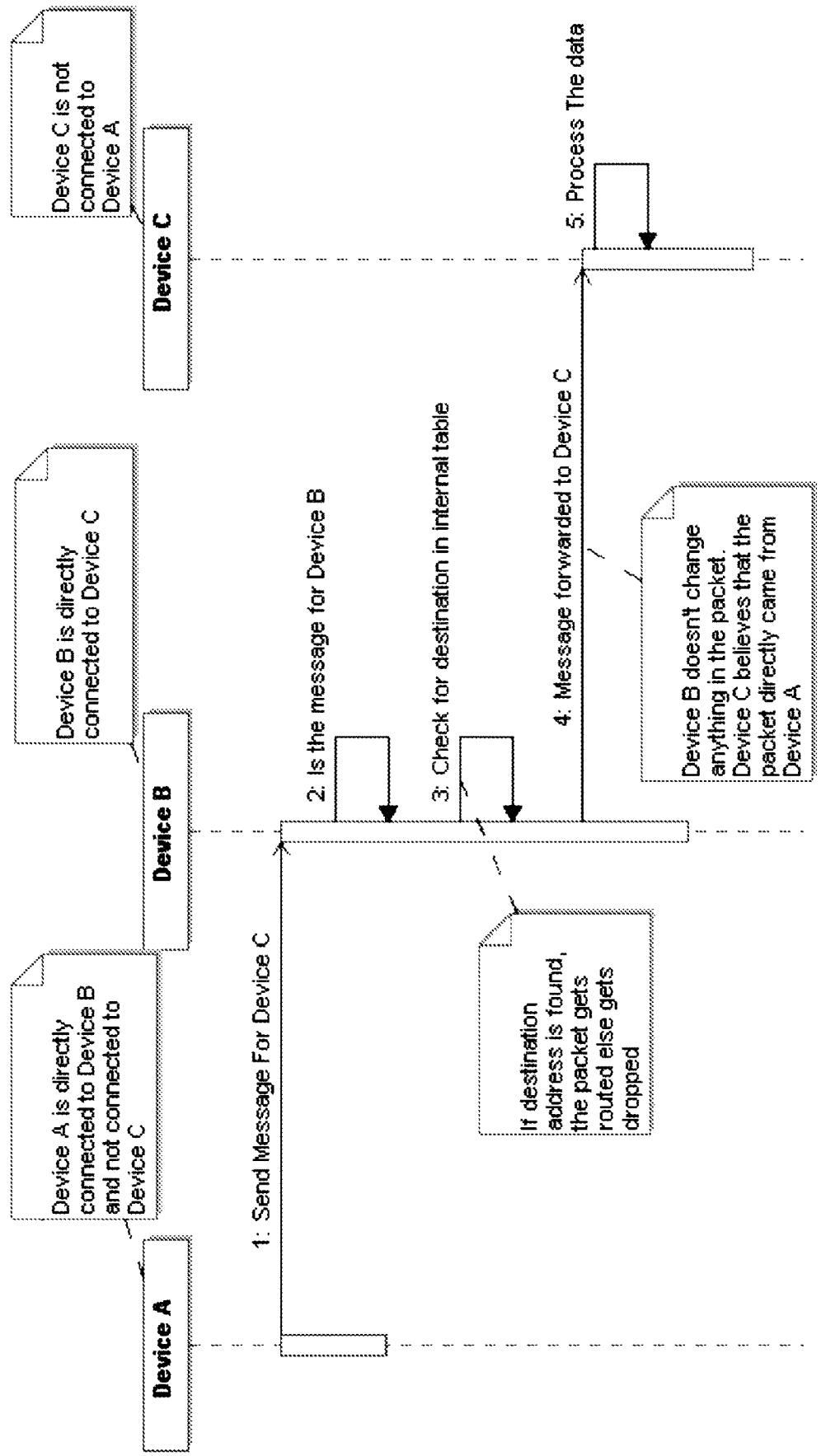
FIG. 9 illustrates an activity diagram showing routing between various devices.

FIG. 9 illustrates an activity diagram showing routing between various devices. As shown, Device A is connected directly to Device B, which is directly connected to Device C. Device A is not directly connect to Device C. When Device A attempts to send a message to Device C, it sends the message out and Device B reads the message, determines that the message is not for the device and checks to see if there is a path to the device in Device B's destination table. If so, Device B forwards the message to Device C, which processes the data. Hence, embodiments of the invention enable routing and daisy chain or multi-bus configurations that are generally not as flexibly possible in medical devices such as infusion pumps.

An embodiment of the manager layer API is detailed below. The manager layer provides the API to enable socket programming over the protocol stack. The manager layer API calls are utilized by any application that wishes to transfer data using an embodiment of the invention.

pro_socket—creates an unbound socket in a communication domain, and returns a file descriptor that can be used in later function calls that operate on sockets.

int16 pro_socket (ConnectionType type, uint8*pSocket)
Arguments:
type: specifies the type of socket to be created (CONNECTIONTYPE and CONNECTIONLESSTYPE for connection oriented and connection-less data exchange).
pSocket: integer pointer to return newly created socket.
typedef enum ConnType

```
{
    CONNECTIONTYPE=1,
    CONNECTIONLESSTYPE=2,
    RAWTYPE=3
} ConnectionType;
```

On successful completion, the function shall return a SUCCESS; else appropriate error code is returned. The API returns allocated socket in the reference variable pSocket passed as a parameter.

pro_bind—assigns a local address to a socket identified by file descriptor socket.
int16 pro_bind (uint8 uint8Socket, const ProSockaddr*pAddress)

```
typedef struct pro_sockaddr
{
    uint8 address;
    uint8 portNo;
    uint8 priority;
    uint8 flags;
    uint32 timeout;
    datafilter *filter;
} ProSockaddr;
``` address: holds logical address of device
portNo: holds port number for connection
priority: holds the priority of the port. All the data passing through this port inherits ports priority
flags: holds configuration flags for changing behavior of socket
TIMEOUT: flag is set, waits for an operation to complete within a given period of time, else returns.
SO_LINGER: set flag indicates that a connection will be terminated only when all the data pending to be sent is sent successfully.
FILTER_DATA: set flag indicates that the data matching supplied filter pattern will only be forwarded to callback function registered to handle it. If flag is reset, data matching the filter will be sent to both, regular socket handler as well as to the registered callback function.
timeout: If the TIMEOUT flag is set, timeout value is specified here. A timeout value of 0 returns immediately.

filter: link list of datafilter type structure defining the filter to be applied on received data. More than one element in this link list will have an ORing property. As an example, if an application wants to process data either from PMC, or UIC, or CE or all three, it will create three nodes in this link list one for each PMC, UIC and CE.

Datafilter structure is used to allow applications to select what messages they want to receive, and which function should handle what type of messages. A regular expression pattern is used to create a filter on received data and once a match is found, data is forwarded to registered callback function.

```
typedef struct
{
    char *regEx;
    uint8 index;
    uint8 length;
    void *callback;
    datafilter *filter;
} datafilter;
``` regEx: pointer to regular expression to be used for matching.
index: location to start looking for match in the data section of received message. A '0' in this field indicates that the match will start from the beginning.
length: staring from the provided index, indicates the length of data section to be considered for regular expression matching. If index contains '0' and length contains '0', match will be performed over the entire data section.
callback: function to be called in case of a successful match. If this field is set to null, all the matching data packets will be dropped depending on FILTER_DATA flag.
filter: linklist of any additional filter to be added over existing filter. If this filed is contains additional filters, on a successful match, callback is made to the function specified in the structure containing this linklist. This link list of filters has anding properties, i.e. a match is successful only if all the regEx specified in all the filters match. As an example, if an application wants to process data containing expressions PMC, UIC and CE, it will instantiate this filter for PMC and have a link list containing filters for UIC and CE respectively.

One or more embodiments support three priority levels for messages namely high, medium and low. The enum defining message priority is as follows.

```
Typedef enum ProPriority
{
    HIGHPRIORITYTYPE = 1,
    MEDIUMPRIORITYTYPE = 2,
    LOWPRIORITYTYPE = 3
} MessagePriority;
```

Arguments:
uint8Socket: file descriptor of socket to be bound
pAddress: pointer to ProSockaddr struct containing address to be bound to the socket.
Return Value:
Upon successful completion, the function shall return SUCCESS, otherwise appropriate error code.
pro_connect—attempts to connect a socket to the specified address.
int16 pro_connect (uint8 uint8Socket, const ProSockaddr *pAddress)

Arguments:
uint8Socket: socket to be connected to specified address.
pAddress: pointer to structure pro_sockaddr containing peer address.
Return Value:
Upon successful completion, the function shall return SUCCESS; otherwise returns appropriate error code
pro_listen—marks the socket referred to by "socket" as a passive socket, that is, as a socket that will be used to accept incoming connection requests using accept( ).
int16 pro_listen (uint8 uint8Socket, uint8 uint8Backlog)
Arguments:
uint8Socket: file descriptor of a socket that needs to be put in accepting connections mode.
uint8Backlog: set a limit on number of outstanding connections in the socket's listen queue. A zero would set the queue length to system defined minimum queue length.
Return Value:
Upon successful completion, the function shall return SUCCESS; otherwise, appropriate error code is returned.
pro_accept—extracts the first connection on the queue of pending connections, creates a new connected socket with same socket type protocol and address family as the specified socket, and returns a new file descriptor for the socket.
int16 pro_accept (uint8 uint8Socket, ProSockaddr *pAddress, uint8 *pClientSocket)
Arguments:
uint8Socket: file descriptor associated with socket.
pAddress: Either a NULL pointer, or a pointer to ProSockaddr struct where the address of connecting socket shall be returned.
pClientSocket: pointer to an unsigned integer for returning file descriptor associated with the newly created socket.
Return Value:
Upon successful completion SUCCESS is returned along with an associated file descriptor for the newly created socket, on failure, returns appropriate error code.
pro_send—initiates transmission of a message from the specified socket to its peer. The pro_send( )function sends a message when the socket is connected.
int16 pro_send (uint8 uint8Socket, const void *pBuffer, uint32 intLength, uint32 *pBytesSent)
Arguments:
uint8Socket: socket's file descriptor
pBuffer: points to buffer containing the message to send.
intLength: length of message in bytes.
pBytesSent: pointer to an integer for returning actual number of bytes sent.
Return Value:
Upon successful completion, the API returns SUCCESS else appropriate error code is returned.
pro_recv—receives a message from a connection-mode or connectionless-mode socket. It is normally used with connected sockets because and does not provide the source address of received data to the application.
int16 pro_recv (uint8 uint8Socket, void *pBuffer, uint32 uintLength, uint32 *pBytesReceived)
Arguments:
uint8Socket: file descriptor of socket.
pBuffer: pointer to the buffer where message should be stored.
uintLength: length in bytes of the message to be received.
pBytesReceived: pointer to an integer for returning number of bytes actually received.
Return Value:
Upon successful completion, SUCCESS is returned along with number of bytes in the reference passed as a parameter, else returns appropriate error code.
pro_close—deallocates the file descriptor and makes the file descriptor available for functions which allocate file descriptors. All outstanding record locks owned by the process on the file associated with the file descriptor are removed. Causes the socket to be destroyed. If the socket is in connection-oriented, and the SO_LINGER option is set for the socket with non-zero linger time, and the socket has un-transmitted data, then pro_close( ) blocks for up to the current linger interval for all pending data to be transmitted.
int16 pro_close (uint8 uint8Socket)
Arguments:
uint8Socket: file descriptor of socket that needs to be closed.
Return Value:
Upon successful completion, function shall return SUCCESS; otherwise appropriate error code shall be returned.
One skilled in the art will recognize that in addition to the exemplary API illustrated above for the Manager Layer, API's for the Session, Transport and Data Link Layers may be implemented as desired to communicate the messages shown in FIGS. 10A-D, 11A-B and 12A-B depending on the desired application.

Figure 13B:
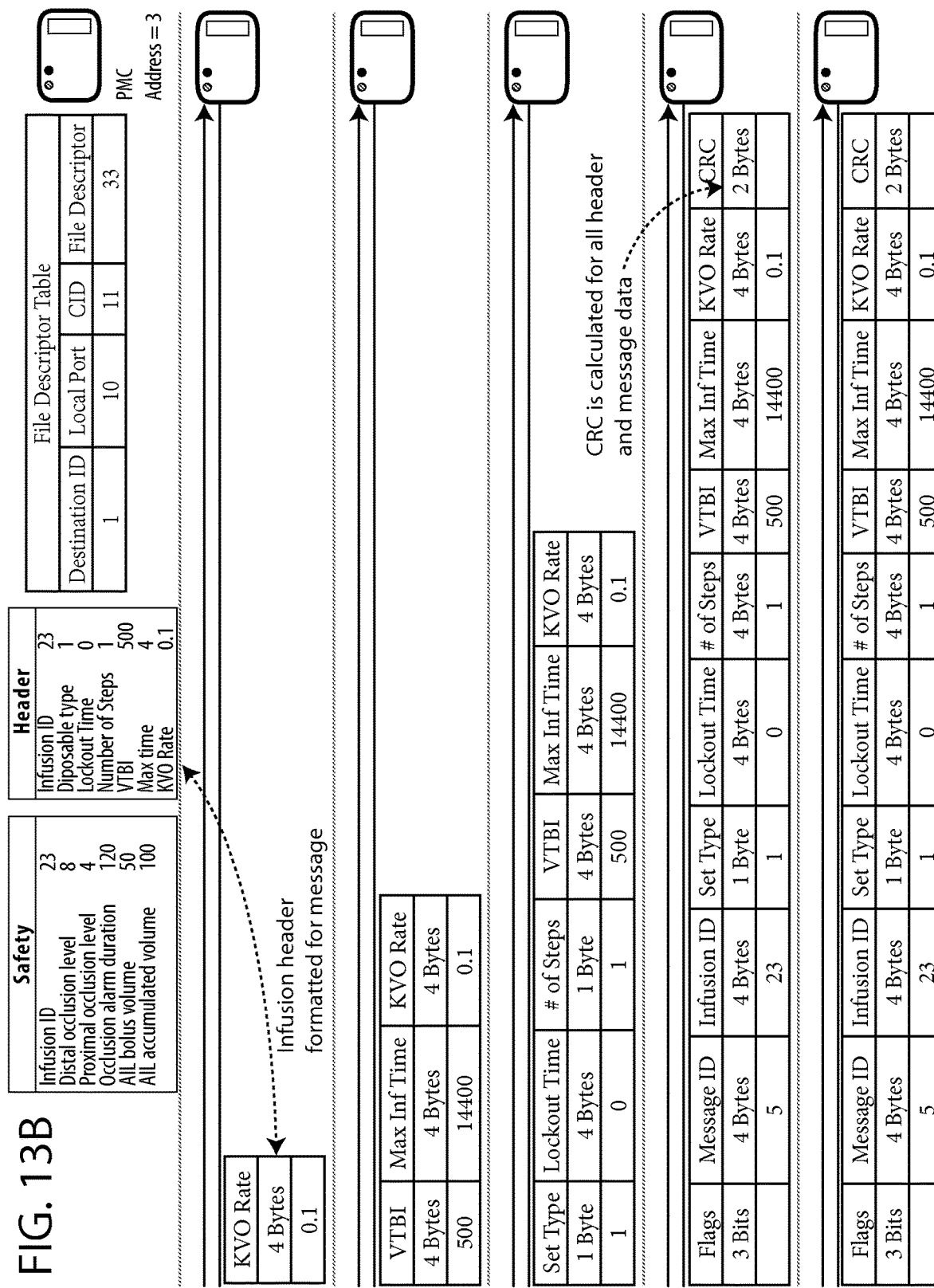

One or more embodiments of the invention may be implemented as a system or method. For example at least one embodiment may include a medical device communication method that includes accepting a request by a programmable device to obtain a device identifier associated with a transmitting device associated with the request, a connection type of connection-oriented or connectionless-oriented, and a receiving device number associated with a receiving device to transmit a message to. The method may also include determining a port number of a port to transmit said message to, for example either via a requesting programmable device or the programmable device that receives the request. Embodiments may also include generating a communication identifier or CID for at least the advantages stated throughout this disclosure. Embodiments may also include accepting a request associated with a medical function, inserting the CID and the medical function into the message, determining if the connection type is connection-oriented or connectionless and transmitting the message to a medical device. This scenario is shown with exemplary values to demonstrate the previous message formatting and transfer in FIGS. 13A and 13B, which are intended to couple with one another on the right side of FIG. 13A and the left side of FIG. 13B.

Embodiments may also include transmitting the message to the receiving device even if the receiving device is not directly connected to the transmitting device. This enables built in routing that allows for devices to pass through messages without requiring a master to control all phases of communication for example.

Embodiments may also include accepting a multicast request configured to enable multiple receiving devices to receive the message. Embodiments may further include accepting a priority parameter configured to enable prioritized handling of the message. This enables messages with high priority to be delivered before other lower priority messages and in one or more embodiments may be implemented with a plurality of message data structures such as queues, linked lists or any other data structure or structures. Embodiments may include transmitting messages from a high priority message queue before transmitting data from a low priority message queue. Other embodiments may apply any type of strategy pattern to the delivery process, and may for example change strategies depending on the type of messages that are likely to be received in particular time periods. This enables predictive handling and processing of messages to provide intelligent and robust delivery of medical functions.

Embodiments may also include determining if a size of data to transfer is larger than a predetermined fragmentation value and packing the data in a plurality of messages to facilitate transfer. Embodiments may efficiently utilize memory and for example reduce latency by copying a pointer to the message between a plurality of message layers without copying the message itself. This is the case since the message does not have to be reconstructed in full within the stack until the full message is received in the application. Furthermore, embodiments of the invention may utilize optimized memory management that includes requesting memory from a buffer that includes non-uniform sizes to further increase efficiency of data memory utilization and lower overall required memory. When sending data packets or message that are larger than the maximum size allowed by the underlying hardware, embodiments may include setting a last fragmentation flag in a final message of fragmented message, starting a timer for an acknowledgement and retransmitting the final message if said timer expires. Further increases in efficiency may be achieved by embodiments that include receiving a request to change a window size for receipt of fragmented messages and adjusting memory usage based thereon, for example having lower window sizes for more reliable communication links. Embodiments may also include providing the device identifier to a new medical device that replaces the medical device after hot-swapping the new medical device for the original medical device, i.e., if a failure occurs. This allows embodiments of the invention to provide robust functionality and transparent replacement of hardware without interrupting medical functions or at least minimizing the interruptions. Embodiments may also include providing a pointer to a complete message after receipt of multiple fragmented messages without copying received message data after receipt thereof. This enables incoming data to be inserted into a buffer once and given to the application after the data is received without extraneous copying for example, which reduces memory utilization and programmable device processing required. One or more embodiments of the invention may include accepting an infusion request associated with an infusion related medical function. Any other type of medical function is in keeping with the spirit of the invention.

Embodiments of the system may include a programmable device configured to accept a request to obtain a device identifier associated with a transmitting device associated with the request, a connection type of connection-oriented or connectionless-oriented, a receiving device number associated with a receiving device to transmit a message to. Embodiments of the system may further determine a port number of a port to transmit said message to, generate a communication identifier or CID and accept a request associated with a medical function. The system may also insert the CID and the medical function into the message, determine if the connection type is connection-oriented or connectionless and transmit the message to a medical device. Embodiments of the system may also implement all functionality of the method previously described and may utilize any of the data structures or API's described herein in combination.

While the invention herein disclosed has been described by means of specific embodiments and applications thereof, numerous modifications and variations could be made thereto by those skilled in the art without departing from the scope of the invention set forth in the claims.

What is claimed is:

1. A communication system for connecting a pump motor controller with a root controller, the communication system comprising:
    a pump motor controller configured to transmit a first message to a root controller, the first message comprising a request for an address;
    a root controller configured to:
        receive the first message;
        determine in a stored table that there is no entry corresponding to the pump motor controller;
        generate a connection identifier for the pump motor controller based on the determination;
        associate the connection identifier in the stored table with the pump motor controller; and
        transmit the connection identifier to the pump motor controller, wherein the pump motor controller is further configured to update its identity with the connection identifier.

2. The communication system of claim 1, wherein the root controller is further configured to facilitate transmission of a second message from the pump motor controller to an additional hardware, wherein the pump motor controller and the additional hardware are not directly connected.

3. The communication system of claim 2, wherein the second message is transferred between a plurality of message layers by copying a pointer and without copying said second message itself.

4. The communication system of claim 2, wherein a session layer communication is made independent of bus topology.

5. The communication system of claim 1, wherein the root controller is further configured to transmit the connection identifier to a second pump motor controller that replaces the pump motor controller.

6. The communication system of claim 1, wherein a fragmented message is reassembled into a complete message in an application buffer.

7. The communication system of claim 1, wherein the root controller is further configured to:
    determine that a size of data to transfer is larger than a predetermined fragmentation value; and
    pack said data in a plurality of messages independent of an underlying data bus width.

8. The communication system of claim 1, wherein the root controller is further configured to request memory from a buffer comprising non-uniform sizes.

9. The communication system of claim 1, wherein the pump motor controller is connected with the root controller without altering an application of the pump motor controller.

10. The communication system of claim 1, wherein a root controller manages connection requests from the plurality of pump motor controllers.

11. A method for connecting hardware components of an infusion pump system, the method comprising:
    receiving a first message corresponding to a first request for an address from a first pump motor controller;
    determining in a stored table that there is no entry corresponding to the first pump motor controller;
    associating a first connection identifier for the first pump motor controller based on the determination;

transmitting the first connection identifier to the first motor controller wherein the first pump motor controller is further configured to update its identity with the first connection identifier;

receiving a second message corresponding to a second request for an address from a second pump motor controller;

determining that the second pump motor controller has replaced the first pump motor controller;

changing the association of the first connection identifier from the first pump moto controller to the second motor controller;

transmitting the first connection identifier to the second motor controller, wherein the second motor controller is further configured to update its identity with the first connection identifier.

12. The method of claim 11, further comprising facilitating transmission of a second message from the pump motor controller to an additional hardware, wherein the pump motor controller and the additional hardware are not directly connected.

13. The method of claim 11, further comprising transmitting messages between hardware components by copying a pointer and without copying the messages.

14. The method of claim 11, wherein a session layer communication is made independent of bus topology.

15. The method of claim 11, wherein a fragmented message is reassembled into a complete message in an application buffer.

16. The method of claim 11, further comprising determining that a size of data to transfer is larger than a predetermined fragmentation value and packing said data in a plurality of messages independent of an underlying data bus width.

17. The method of claim 11, further comprising requesting memory from a buffer comprising non-uniform sizes.

* * * * *